(12) United States Patent
Datta et al.

(10) Patent No.: US 12,176,099 B2
(45) Date of Patent: Dec. 24, 2024

(54) LOW-COST ESTIMATION AND/OR TRACKING OF INTRA-SCAN FOCAL-SPOT DISPLACEMENT

(71) Applicant: GE Precision Healthcare LLC, Wauwatosa, WI (US)

(72) Inventors: Arka Datta, Pewaukee, WI (US); Adam Israel Cohen, Milwaukee, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 418 days.

(21) Appl. No.: 17/657,411

(22) Filed: Mar. 31, 2022

(65) Prior Publication Data
US 2023/0317264 A1  Oct. 5, 2023

(51) Int. Cl.
| | | |
|---|---|---|
| *G16H 40/40* | (2018.01) | |
| *A61B 6/00* | (2024.01) | |
| *A61B 6/40* | (2024.01) | |
| *A61B 6/42* | (2024.01) | |

(52) U.S. Cl.
CPC ........... *G16H 40/40* (2018.01); *A61B 6/4021* (2013.01); *A61B 6/4035* (2013.01); *A61B 6/4266* (2013.01)

(58) Field of Classification Search
CPC .... G16H 40/40; A61B 6/4021; A61B 6/4035; A61B 6/4266
See application file for complete search history.

(56) References Cited

U.S. PATENT DOCUMENTS

| | | |
|---|---|---|
| 6,968,039 B2 | 11/2005 | Lemaitre et al. |
| 8,891,727 B2 | 11/2014 | Kurochi et al. |
| 10,383,203 B2 | 8/2019 | Meiler et al. |
| 11,141,128 B2 | 10/2021 | Jacob et al. |

(Continued)

OTHER PUBLICATIONS

Flay, N. et al. | "Investigation of the focal spot drift in industrial cone-beam X-ray computed tomography. Digital Industrial Radiology and Computed Tomography". Digital Industrial Radiology and Computed Tomography (DIR 2015) Jun. 22-25, 2015, Belgium, Ghent—www.ndt.net/app.DIR2015, 10 pages.

(Continued)

*Primary Examiner* — David F Dunphy
(74) *Attorney, Agent, or Firm* — Amin, Turocy & Watson, LLP

(57) ABSTRACT

Systems/techniques that facilitate low-cost estimation and/or tracking of intra-scan focal-spot displacement are provided. In various embodiments, a system can cause a medical imaging scanner to perform an air scan. In various aspects, the system can access data produced by the medical imaging scanner and relating to the air scan, where the data can include a set of gantry angles swept by an X-ray tube during the air scan, where the data can include a set of intensity value matrices recorded by a multi-channel-multi-row detector during the air scan, and where the set of intensity value matrices respectively correspond to the set of gantry angles. In various instances, the system can compute a set of channel-spanning intensity slopes based on the set of intensity value matrices. In various cases, the system can apply a slope-to-displacement transfer function to the set of channel-spanning intensity slopes, thereby yielding a set of focal-spot displacements.

20 Claims, 23 Drawing Sheets

(56) References Cited

U.S. PATENT DOCUMENTS

2015/0103972 A1\* 4/2015 Bredno ................ A61B 6/583
378/7
2020/0222024 A1 7/2020 Edic et al.
2022/0296202 A1\* 9/2022 Zhan ................... A61B 6/4241

OTHER PUBLICATIONS

GE Patent Application CT x-ray tube alignment by electronic methods, IPCOM000199661D, (assignee: GE Healthcare), 2010, 8 pages.
Notice of Allowance received for U.S. Appl. No. 17/657,692, dated Jun. 24, 2024, 29 pages.

\* cited by examiner

LOW-COST ESTIMATION AND/OR TRACKING OF INTRA-SCAN FOCAL-SPOT DISPLACEMENT

TECHNICAL FIELD

The subject disclosure relates generally to focal-spots of medical imaging devices, and more specifically to low-cost estimation and/or tracking of intra-scan focal-spot displacement.

BACKGROUND

Within an X-ray tube of a medical imaging device, an electron beam is accelerated from a cathode to an anode, so as to produce X-rays. The area over which the electron beam strikes the anode is referred to as the focal-spot. Image artefacts can occur when the focal-spot is at an undesirable and/or unintended location. Correcting or preventing such image artefacts can depend upon tracking how the focal-spot of the medical imaging device moves during a medical imaging scan.

Systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate low-cost estimation and/or tracking of intra-scan focal-spot displacement are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a scan component that can cause a medical imaging scanner to perform an air scan, where the medical imaging scanner can have an X-ray tube, a gantry, and/or a multi-channel-multi-row detector. In various aspects, the computer-executable components can further comprise a receiver component that can access data produced by the medical imaging scanner and relating to the air scan, where the data can include a set of gantry angles swept by the X-ray tube during the air scan, where the data can include a set of intensity value matrices recorded by the multi-channel-multi-row detector during the air scan, and/or where the set of intensity value matrices respectively can correspond to the set of gantry angles. In various instances, the computer-executable components can further comprise a slope component that can compute a set of channel-spanning intensity slopes based on the set of intensity value matrices, where the set of channel-spanning intensity slopes can respectively correspond to the set of gantry angles. In various cases, the computer-executable components can further comprise a displacement component that can apply a slope-to-displacement transfer function to the set of channel-spanning intensity slopes, thereby yielding a set of focal-spot displacements that can respectively correspond to the set of gantry angles. In various aspects, the computer-executable components can further comprise an execution component that can initiate one or more electronic actions based on the set of focal-spot displacements.

According to one or more embodiments, the above-described system can be implemented as a computer-implemented method and/or a computer program product.

DETAILED DESCRIPTION

Figure 1:
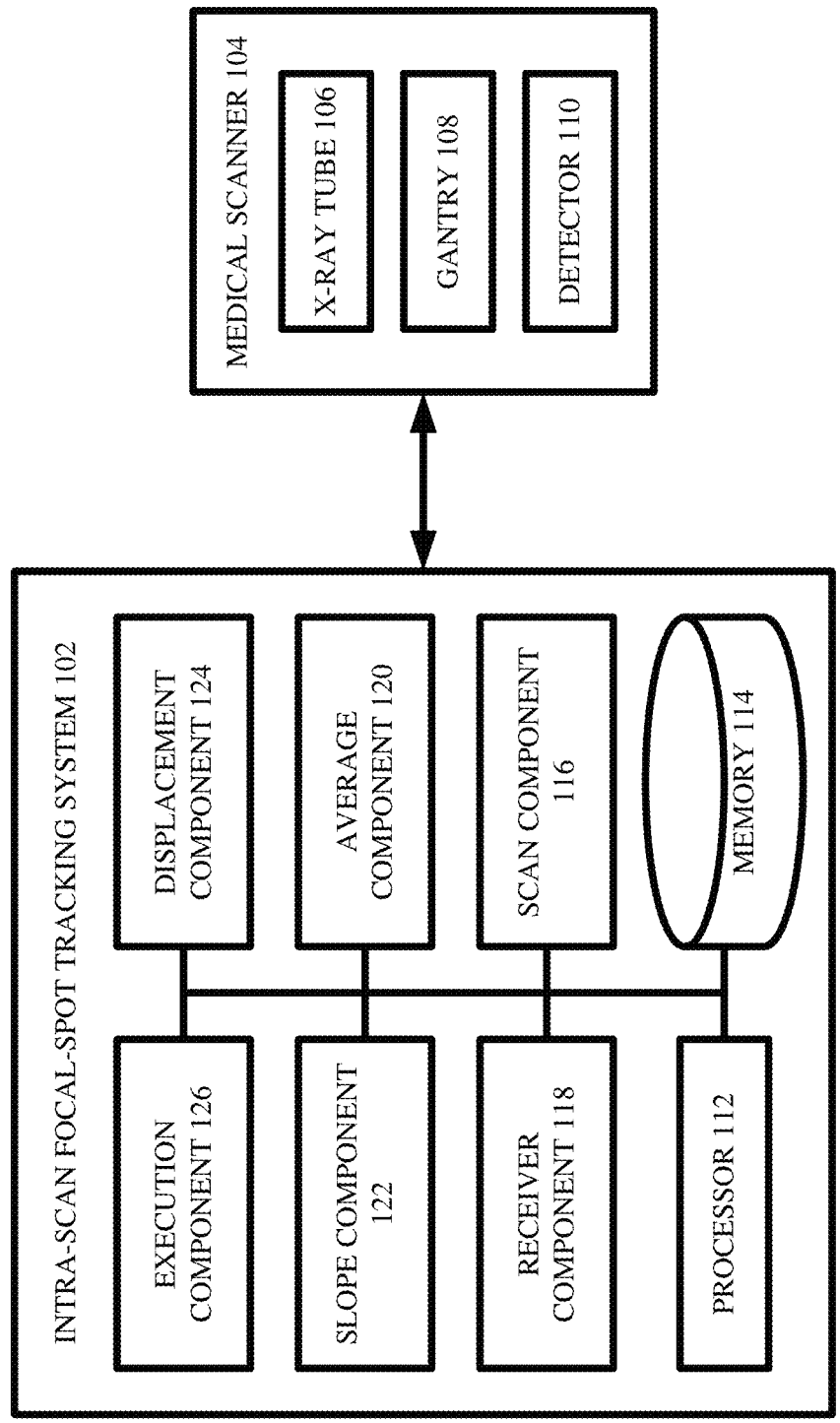
FIG. 1 illustrates a block diagram of an example, non-limiting system that facilitates low-cost estimation and/or tracking of intra-scan focal-spot displacement in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Within an X-ray tube of a medical imaging device (e.g., a computed tomography (CT) scanner), an electron beam can be accelerated from a cathode to an anode. As the electron beam strikes the anode, X-rays can be produced. The surface area over which the electron beam strikes can be referred to as the focal-spot (e.g., the focal-spot of the X-ray tube, and/or the focal-spot of the medical imaging device). Imaging artefacts (e.g., shadows, streaks, band, ring) can occur when the position of the focal-spot undesirably and/or unintentionally changes. Correcting or preventing such imaging artefacts can depend upon tracking how the focal-spot of the medical imaging device moves during a medical imaging scan.

For example, the X-ray tube of the medical imaging device can rotate about and/or along a gantry of the medical imaging device. Accordingly, a medical imaging scan (e.g., a scanning protocol) can involve sweeping the X-ray tube of the medical imaging device through a set of gantry angles (e.g., through an angular interval about/along the gantry). At each gantry angle, the X-ray tube can emit one or more X-rays that can pass diametrically and/or radially through a bore of the gantry, and such one or more X-rays can be captured/recorded by a detector (e.g., a multi-channel and/or multi-row detector) that rotates about/along the gantry so as to maintain angular opposition to the X-ray tube. Thus, at each gantry angle, the detector can be considered as capturing/recording a unique "view" of whatever object (e.g., anatomical structure of a medical patient) is currently placed in the bore of the gantry.

Unfortunately, the focal-spot of the X-ray tube can unintentionally change position (e.g., can shift and/or drift) as the X-ray tube rotates about/along the gantry. Such unintentional motion of the focal-spot can be due to any number of reasons, such as due to Earth's magnetic field interacting differently with the electron beam of the X-ray tube at different gantry angles, and/or due to gravity interacting differently with the anode and/or cathode of the X-ray tube at different gantry angles. In any case, the position of the focal-spot can experience changes from gantry angle to gantry angle. Such changes in focal-spot position can be referred to as intra-scan focal-spot displacements (e.g., since a single scan can involve sweeping the X-ray tube through multiple gantry angles). Such intra-scan focal-spot displacements can cause the medical imaging device to produce significant imaging artefacts, which can be undesirable.

To help correct, prevent, and/or otherwise reduce such imaging artefacts, it can be beneficial to estimate and/or track such intra-scan focal-spot displacements. In other words, before such imaging artefacts can be remedied, it can be beneficial to know how and/or where the focal-spot moves during/throughout a scan. Those having ordinary skill in the art will appreciate that the instantaneous position of the focal-spot of the X-ray tube can be experimentally determined via any suitable tungsten edge measurement technique. However, it would be exceedingly burdensome, time-consuming, and/or resource-intensive to implement such tungsten edge measurement technique for each possible gantry angle to which the X-ray tube can rotate. After all, an X-ray tube can typically rotate through a 360-degree interval about/along a gantry, and such 360-degree interval can typically be broken up into hundreds or even thousands of gantry angles (e.g., hundreds and/or thousands of locations about/along the gantry to which the X-ray tube can rotate). Performing a tungsten edge measurement at each of such hundreds and/or thousands of gantry angles (e.g., at each of such hundreds and/or thousands of views) can be undesirable.

Moreover, intra-scan focal-spot displacements can depend not just upon gantry angle, but also upon other configurable parameters of the medical imaging device (e.g., anode-cathode voltage of the medical imaging device, anode-cathode amperage of the medical imaging device, type of filter used by the medical imaging device, size of the focal-spot of the medical imaging device). There can be tens of thousands of different ways in which the possible gantry angles of the medical imaging device can combine and/or permute with the possible parameter configurations of the medical imaging device. Performing a tungsten edge measurement at each of such tens of thousands of combinations/permutations would certainly be excessively burdensome.

Accordingly, systems and/or techniques that can address one or more of these technical problems can be desirable.

Various embodiments described herein can address one or more of these technical problems. One or more embodiments described herein can include systems, computer-implemented methods, apparatus, and/or computer program products that can facilitate low-cost estimation and/or tracking of intra-scan focal-spot displacement. That is, the inventors of various embodiments described herein devised a technique that can track, monitor, and/or otherwise compute intra-scan focal-spot displacements of a medical imaging device, which technique does not include the burdensome cost of applying a tungsten edge measurement at each possible combination/permutation of gantry angle and configurable parameter. In particular, the present inventors devised a novel metric and/or characteristic that can be computed for a medical imaging device, which novel metric/characteristic can be leveraged to facilitate low-cost estimation/tracking of intra-scan focal-spot displacement. In various cases, such novel metric/characteristic can be channel-spanning intensity slope, as described herein.

More specifically, and as mentioned above, when an X-ray tube of a medical imaging device emits X-rays from a particular gantry angle (e.g., from a particular location about/along the gantry of the medical imaging device), such X-rays can be captured/recorded by a detector of the medical imaging device. Because the detector can exhibit a multi-channel and/or multi-row architecture, the output of the detector for that particular gantry angle can be an intensity value matrix. In other words, the output can be a matrix of Hounsfield unit values, with each Hounsfield unit value corresponding to a specific row and a specific channel of the detector. In various aspects, the present inventors recognized that a slope of such Hounsfield unit values can be calculated and/or approximated across any suitable interval of channels of the detector. Furthermore, the present inventors realized that the value of such slope, which can be referred to as a channel-spanning intensity slope, can be closely correlated with the position of the focal-spot of the X-ray tube of the medical imaging device. That is, the present inventors realized that the position of the focal-spot of the medical imaging device can be accurately predicted and/or inferred when given a known channel-spanning intensity slope of the medical imaging device. Further still, it can be much less time-consuming, much less resource-intensive, and/or much less burdensome to calculate a channel-spanning intensity slope at each possible combination/permutation of gantry angle and configurable parameter of the medical imaging device, as compared to performing a tungsten edge measurement at each of such possible combinations/permutations. Accordingly, the present inventors devised various systems and/or techniques described herein, which can estimate and/or track, in low-cost and/or low-burden fashion, intra-scan focal-spot displacements by leveraging channel-spanning intensity slopes.

In various aspects, various embodiments described herein can be considered as a computerized tool (e.g., any suitable combination of computer-executable hardware and/or computer-executable software) that can facilitate low-cost estimation and/or tracking of intra-scan focal-spot displacement. In various aspects, the computerized tool can comprise a scan component, a receiver component, an average component, a slope component, a displacement component, and/or an execution component.

In various embodiments, there can be a medical scanner that includes an X-ray tube, a gantry, and/or a detector. In various aspects, the medical scanner can be any suitable type of medical imaging device as desired (e.g., a CT scanner). In any case, the X-ray tube of the medical scanner can rotate about/along the gantry (e.g., in some cases, the X-ray tube can rotate 360 degrees about the gantry; in other cases, the X-ray tube can rotate through any other suitable angular interval about the gantry). In various instances, the detector of the medical scanner can also rotate about/along the gantry, such that the detector maintains angular opposition with the X-ray tube (e.g., such that the X-ray tube and the detector face each other across the bore of the gantry).

In various aspects, the medical scanner can have various controllable and/or configurable settings/parameters. In various instances, a controllable/configurable setting/parameter of the medical scanner can be gantry angle (e.g., measured in degrees and/or radians). In other words, such controllable/configurable setting/parameter can be considered as the angular location about/along the gantry to which the X-ray tube rotates. As those having ordinary skill in the art will appreciate, a scan (e.g., a scanning protocol) that is performed by the medical scanner can involve sweeping the X-ray tube through multiple gantry angles (e.g., through any suitable angular interval about/along the gantry).

In various cases, another controllable/configurable setting/parameter of the medical scanner can be anode-cathode voltage and/or anode-cathode amperage. That is, such controllable/configurable setting/parameter can be the electric voltage (e.g., measured in peak kilovolts) and/or the electric amperage (e.g., measured in milliamps) that is applied to the X-ray tube so as to accelerate the electron beam from the cathode to the anode. As those having ordinary skill in the art will appreciate, a scan (e.g., a scanning protocol) that is performed by the medical scanner can involve sweeping the X-ray tube through multiple gantry angles while the X-ray tube is held at a constant anode-cathode voltage/amperage. However, in other cases, a scan (e.g., a scanning protocol) that is performed by the medical scanner can involve sweeping the X-ray tube through multiple gantry angles with a varying anode-cathode voltage/amperage (e.g., such that a different anode-cathode voltage/amperage is applied in the X-ray tube at different gantry angles).

In various aspects, still another controllable/configurable setting/parameter of the medical scanner can be a type of filter that is implemented in the X-ray tube. For example, the X-ray tube can, in some cases, use a flat filter, and/or can, in other cases, use a bowtie filter.

In various instances, yet another controllable/configurable setting/parameter of the medical scanner can be a size of the focal-spot of the X-ray tube. That is, such controllable/configurable setting/parameter can be the diameter and/or radius (e.g., measured in microns and/or millimeters) of the portion of the surface area of the anode which is struck and/or impacted by the electron beam. As those having ordinary skill in the art will appreciate, a scan (e.g., a scanning protocol) that is performed by the medical scanner can involve sweeping the X-ray tube through multiple gantry angles while the X-ray tube is held at a constant focal-spot size. However, in other cases, a scan (e.g., a scanning protocol) that is performed by the medical scanner can involve sweeping the X-ray tube through multiple gantry angles with a varying focal-spot size (e.g., such that a different focal-spot size is generated in the X-ray tube at different gantry angles).

In any case, it can be desired to estimate and/or track intra-scan focal-spot displacement of the medical scanner. In other words, it can be desired to determine how/where the focal-spot of the X-ray tube moves as the X-ray tube rotates about the gantry. The computerized tool described herein can facilitate such estimation and/or tracking.

In various embodiments, the scan component of the computerized tool can electronically instruct and/or command the medical scanner to perform an air scan. That is, with no object and/or anatomical structure of a medical patient being placed in the bore of the gantry (e.g., with only air in the bore of the gantry), the scan component can electronically cause the medical scanner to sweep the X-ray tube through a set of gantry angles, where the X-ray tube can emit X-rays from each gantry angle, and where the detector can capture/record such X-rays for each gantry angle.

In various embodiments, the receiver component of the computerized tool can electronically receive and/or otherwise electronically access air scan data produced during and/or in response to the air scan by the detector. In some instances, the receiver component can electronically retrieve the air scan data from any suitable centralized and/or decentralized data structure (e.g., graph data structure, relational data structure, hybrid data structure), whether remote from and/or local to the receiver component. In other instances, the receiver component can electronically retrieve the air scan data from the medical scanner itself. In any case, the receiver component can electronically obtain and/or access the air scan data, such that other components of the computerized tool can electronically interact with (e.g., read, write, edit, manipulate) the air scan data.

In various aspects, the air scan data can indicate/include the set of gantry angles through which the X-ray tube is swept during the air scan. In some cases, the set of gantry angles can be considered as a set of "views" about/along the gantry. In various instances, the air scan data can further indicate/include a set of intensity value matrices that respectively correspond (e.g., in one-to-one fashion) to the set of gantry angles. More specifically, for each particular gantry angle to which the X-ray tube is rotated during the air scan, the detector can generate/produce a particular intensity value matrix (e.g., a matrix of Hounsfield unit values), where the particular intensity value matrix can be considered as the result of the detector recording/capturing X-rays emitted by the X-ray tube from the particular gantry angle. As those having ordinary skill in the art will appreciate, the dimensionality of an intensity value matrix can depend upon the physical architecture of the detector. For example, if the detector exhibits a multi-channel and multi-row structure that has a channels and b rows, for any suitable positive integers a and b, then each intensity value matrix can be an a-by-b matrix (e.g., or a b-by-a matrix) of Hounsfield unit values, where each Hounsfield unit value can respectively correspond to a certain channel and a certain row of the detector.

In various embodiments, the average component of the computerized tool can electronically compute a set of row-averaged intensity value vectors based on the set of row-averaged intensity value matrices. In various aspects, the set of row-averaged intensity value vectors can respectively correspond (e.g., in one-to-one fashion) to the set of intensity value matrices and thus to the set of gantry angles. For example, for any given intensity value matrix, the average component can calculate/compute an intensity value vector based on that given intensity value matrix. Since that given intensity value matrix can correspond to a particular gantry angle, the calculated/computed intensity value vector can be considered as also corresponding to that particular gantry angle. In any case, the average component can calculate/compute the intensity value vector by averaging across and/or averaging-out the rows of the given intensity value matrix.

For instance, as mentioned above, when the detector of the medical scanner has a channels and b rows, an intensity value matrix produced by the detector can be an a-by-b matrix of Hounsfield unit values. For ease of explanation, suppose that an element (i,j) of the intensity value matrix, where i is an integer between 1 and a inclusively, and where j is an integer between 1 and b inclusively, can be a Hounsfield unit value recorded by the i-th channel and the j-row of the detector. In various aspects, the average component can compute a first average intensity value of Hounsfield unit values recorded across all rows by the first channel (e.g., $1/b\Sigma_{j=1}^{b}I(1,j)$, where $I(1,j)$ can be the Hounsfield unit value recorded by the first channel and the j-th row of the detector). Similarly, the average component can compute an a-th average intensity value of Hounsfield unit values recorded across all rows by the a-th channel (e.g., $1/b\Sigma_{j=1}^{b}I(a,j)$, where $I(a,j)$ can be the Hounsfield unit value recorded by the a-th channel and the j-th row of the detector). Accordingly, the first average intensity value to the a-th average intensity value can be considered as collectively forming a vector having a total of a elements. Such vector can be referred to as a row-averaged intensity value vector.

In any case, the average component can electronically calculate a set of row-averaged intensity value vectors based on the set of intensity value matrices (e.g., can compute one row-averaged intensity value vector per intensity value matrix).

In various embodiments, the slope component of the computerized tool can electronically compute a set of channel-spanning intensity slopes based on the set of row-averaged intensity value vectors. In various aspects, the set of channel-spanning intensity slopes can respectively correspond (e.g., in one-to-one fashion) to the set of row-averaged intensity value vectors and thus to the set of gantry angles. For example, for any given row-averaged intensity value vector, the slope component can calculate/compute a channel-spanning intensity slope based on that given row-averaged intensity value vector. Since that given row-averaged intensity value vector can correspond to a particular gantry angle, the calculated/computed channel-spanning intensity slope can be considered as also corresponding to that particular gantry angle. In any case, the slope component can calculate/compute the channel-spanning intensity slope by fitting a trendline to the given row-averaged intensity value vector.

For instance, as mentioned above, when the detector of the medical scanner has a channels and b rows, a row-averaged intensity value vector can be an a-element vector of row-averaged Hounsfield unit values. For ease of explanation, suppose that an element (i) of the row-averaged intensity value vector, where i is an integer between 1 and a inclusively, can be a scalar that is yielded by averaging Hounsfield unit values recorded by the i-th channel of the detector across all b rows of the detector. In other words, the row-averaged intensity value vector can be considered as having one element per channel of the detector. In various aspects, the slope component can select any suitable interval of elements, and thus any suitable interval of channels, in the row-averaged intensity value vector. In some cases, the interval can be all a elements (and thus all a channels) in the row-averaged intensity value vector (e.g., the interval can extend from the first channel to the a-th channel). In other cases, the interval can be fewer than all a elements (and thus fewer than all a channels) in the row-averaged intensity value vector (e.g., the interval can extend from a q-th channel to an r-th channel, where q and r can be integers such that $1 \leq q < r \leq a$). In any case, once the interval of elements (e.g., once the channel interval) is selected, the slope component can plot such interval of elements in a graph and/or can fit a linear trendline to such plot. In various aspects, the slope of such linear trendline, which can have units and/or dimensions of Hounsfield unit per channel, can be referred to as a channel-spanning intensity slope.

In any case, the slope component can electronically calculate a set of channel-spanning intensity slopes based on the set of row-averaged intensity value vectors (e.g., can compute one channel-spanning intensity slope per row-averaged intensity value vector).

In various embodiments, the displacement component of the computerized tool can electronically compute a set of focal-spot displacements based on the set of channel-spanning intensity slopes. In various aspects, the set of focal-spot displacements can respectively correspond (e.g., in one-to-one fashion) to the set of channel-spanning intensity slopes and thus to the set of gantry angles. For example, for any given channel-spanning intensity slope, the displacement component can calculate/compute a focal-spot displacement (e.g., measured in microns and/or millimeters from a predetermined/desired focal-spot position and/or along any suitable axis/direction) based on that given channel-spanning intensity slope. Since that given channel-spanning intensity slope can correspond to a particular gantry angle, the calculated/computed focal-spot displacement can be considered as also corresponding to that particular gantry angle.

In various cases, the displacement component can calculate/compute the focal-spot displacement by applying a slope-to-displacement transfer function to the given channel-spanning intensity slope. In various aspects, the slope-to-displacement transfer function can be any suitable mathematical function and/or combination of mathematical functions that takes as an argument a channel-spanning intensity slope value (e.g., and/or a change in channel-spanning intensity slope value) and that produces as output a focal-spot displacement value (e.g., a change in position of the focal-spot of the X-ray tube as measured along any suitable axis and/or direction). In various instances, the slope-to-displacement transfer function can be obtained experimentally, as explained in more detail herein.

In any case, because the set of focal-spot displacements can correspond to the set of gantry angles, the set of focal-spot displacements can be considered as describing how and/or where the focal-spot of the medical scanner moves as the X-ray tube rotates about/along the gantry. In other words, the set of focal-spot displacements can be considered as describing and/or representing the intra-scan focal-spot motion of the medical scanner (e.g., can be considered as a set of intra-scan focal-spot displacements).

In various embodiments, the execution component of the computerized tool can electronically initiate and/or perform one or more electronic actions based on the set of focal-spot displacements. As a non-limiting example, the execution component can, in some aspects, electronically plot, on any suitable electronic display/monitor/screen, the set of focal-spot displacements against the set of gantry angles. Accordingly, a medical professional can visually look at such plot so as to see how the position of the focal-spot of the medical scanner changes with gantry angle. As another non-limiting example, the execution component can, in various cases, electronically generate and/or electronically transmit a maintenance recommendation based on the set of focal-spot displacements. For instance, the execution component can compare the set of focal-spot displacements to any suitable threshold value, and if the set of focal-spot displacements fail to satisfy the threshold value (e.g., if a largest focal-spot in the set is higher than a maximum allowable displacement threshold), then the execution component can recommend that the medical scanner should undergo maintenance. Indeed, in some cases, the execution component can automatically schedule a maintenance visit for the medical scanner if the set of focal-spot displacements fail to satisfy the threshold value.

In any case, the set of focal-spot displacements, which can respectively correspond to the set of gantry angles, can be considered as representing and/or describing the intra-scan focal-spot motion of the medical scanner.

In order to accurately identify the set of focal-spot displacements, it can be necessary to first identify the slope-to-displacement transfer function. In various aspects, the slope-to-displacement transfer function can depend upon the medical scanner itself and can thus be obtained experimentally and/or in a laboratory setting as follows.

First, a baseline channel-spanning slope of the medical scanner can be obtained. In order to obtain the baseline channel-spanning slope, a partial air scan can be performed by the medical scanner. That is, with nothing but air in the gantry bore, the X-ray tube can emit X-rays from any single gantry angle, and the detector can record/capture such X-rays, thereby yielding a single intensity value matrix. Because such intensity value matrix can be the result of a partial air scan, it can be referred to as an air-based intensity value matrix. In various aspects, row-averaging (as described above) can be performed on the air-based intensity value matrix, thereby yielding a row-averaged intensity value vector. Because such row-averaged intensity value vector is based on the partial air scan, it can be referred to as an air-based row-averaged intensity value vector. In various instances, a channel-spanning slope can be computed (as described above) by plotting and fitting a linear trendline to any suitable interval of the air-based row-averaged intensity value vector. Such channel-spanning slope can be referred to as the baseline channel-spanning slope of the medical scanner.

Next, a baseline focal-spot position of the medical scanner can be obtained. In order to obtain the baseline focal-spot position, a partial edge scan can be performed by the medical scanner. That is, with nothing but air in the gantry bore, and with a tungsten edge placed between the anode and the cathode, the X-ray tube can emit X-rays from the same gantry angle used for the baseline channel-spanning slope, and the detector can capture/record such X-rays, thereby yielding a single intensity value matrix. Because such intensity value matrix can be the result of a partial edge scan, it can be referred to as an edge-based intensity value matrix. In various aspects, normalization can be facilitated by dividing, in element-wise fashion, the edge-based intensity value matrix by the air-based intensity value matrix, thereby yielding a normalized edge-based intensity value matrix. As those having ordinary skill in the art will appreciate, a point-spread function can be derived from the normalized edge-based intensity value matrix (e.g., a line-spread function can be derived first, and then the point-spread function can be derived from the line-spread function). Because the point-spread function can be considered as a multi-dimensional Gaussian distribution, the centroid of the point-spread function can be considered as representing the focal-spot of the medical scanner. Accordingly, the position of the centroid of the point-spread function can be considered as the baseline focal-spot position of the medical scanner.

Now, for any suitable number of iterations, the focal-spot of the medical scanner can be perturbed by injection of a known positional shift, and both a perturbed channel-spanning slope and a perturbed focal-spot position can be obtained as described above (e.g., in the same way that the baseline channel-spanning slope and the baseline focal-spot position are obtained). For example, after injection of the known positional shift, the perturbed channel-spanning slope can be obtained by: performing a partial air scan at the same gantry angle mentioned above, thereby yielding a perturbed air-based intensity value matrix; row-averaging the perturbed air-based intensity value matrix, thereby yielding a perturbed air-based row-averaged intensity value vector; and plotting and fitting a linear trendline to the perturbed air-based row-averaged intensity value vector, thereby yielding the perturbed channel-spanning slope. Moreover, after injection of the known positional shift, the perturbed focal-spot position can be obtained by: performing a partial edge scan at the same gantry angle mentioned above, thereby yielding an edge-based intensity value matrix; normalizing the perturbed edge-based intensity value matrix by dividing by the perturbed air-based intensity value matrix, thereby yielding a normalized perturbed edge-based intensity value matrix; and deriving a perturbed point-spread function from the normalized perturbed edge-based intensity value matrix, where the position of the centroid of the perturbed point-spread function can be considered as the perturbed focal-spot position.

In various aspects, such perturbations (e.g., such injection of known positional shifts) can be performed for any suitable number of iterations (e.g., with a different and/or unique positional shift being injected at each iteration), thereby yielding a set of perturbed channel-spanning slopes and a set of perturbed focal-spot positions that can respectively correspond to each other.

Next, a set of changes in channel-spanning slope can be computed by subtracting the baseline channel-spanning slope from each of the set of perturbed channel-spanning slopes. Similarly, a set of perturbed focal-spot displacements can be computed by subtracting the baseline focal-spot position from each of the set of perturbed focal-spot positions. Note that the set of perturbed focal-spot displacements can be considered as respectively corresponding (e.g., in one-to-one fashion) to the set of changes in channel-spanning slope.

In various instances, the set of perturbed focal-spot displacements can be plotted against the set of changes in channel-spanning slope, and any suitable trendline (e.g., linear, quadratic, exponential, logarithmic, polynomial) can be fitted to such plot. In various aspects, such trendline can be considered as the slope-to-displacement transfer function, since such trendline can take as an argument a change in channel-spanning slope and can produce as output a focal-spot displacement. Accordingly, in this way, the slope-to-displacement transfer function can be experimentally obtained.

As those having ordinary skill in the art will appreciate, the slope-to-displacement transfer function can depend upon the controllable/configurable parameters/settings of the medical scanner. For example, the above-described experimental procedure can be performed when the medical scanner is configured to utilize a particular anode-cathode voltage/amperage, a particular filter, and/or a particular focal-spot size, thereby yielding a particular slope-to-displacement transfer function. In various cases, the above-described experimental procedure can be repeated when the medical scanner is configured to utilize a different anode-cathode voltage/amperage, a different filter, and/or a different focal-spot size, thereby yielding a different slope-to-displacement transfer function. In this way, different transfer functions can be obtained for different configurations of the medical scanner.

Note that, in various aspects, the number of tungsten edge measurements (e.g., the number of partial edge scans) performed to obtain the slope-to-displacement transfer function can be significantly lower than the number of tungsten edge measurements that would be needed if one tungsten edge measurement were instead performed at every possible gantry angle of the medical scanner. Indeed, as mentioned above, there can often be hundreds or even thousands of gantry angles about/along a gantry of a medical scanner. Thus, tracking intra-scan focal-spot displacement only via tungsten edge measurements would require performing hundreds or even thousands of such tungsten edge measurements (e.g., performing one partial edge scan at each gantry angle). This would be excessively time-consuming and burdensome. Moreover, such costs/burdens would be exacerbated by the added variability of the other configurable/controllable parameters/settings of the medical scanner (e.g., a unique tungsten edge measurement would be needed for each unique combination of gantry angle, anode-cathode voltage/amperage, type of filter, and/or focal-spot size).

In stark contrast, the slope-to-displacement transfer function described herein can be obtained using far fewer tungsten edge measurements. Indeed, for any given anode-cathode voltage/amperage, for any given filter, and/or for any given focal-spot size, an accurate slope-to-displacement transfer function can be obtained with as few as tens and/or dozens of tungsten edge measurements (e.g., tens/dozens of partial edge scans, tens/dozens of perturbations). In other words, estimating and/or tracking intra-scan focal-spot displacement via a slope-to-displacement transfer function as described herein can be far less costly in terms of time, effort, and/or other resources, as compared to estimating/tracking intra-scan focal-spot displacement via only tungsten edge measurements.

Accordingly, various embodiments described herein can be considered as a computerized tool that can electronically estimate/track, in low-cost fashion, intra-scan focal-spot displacement of a medical scanner, by leveraging channel-spanning intensity slope and/or a slope-to-displacement transfer function.

Various embodiments described herein can be employed to use hardware and/or software to solve problems that are highly technical in nature (e.g., to facilitate low-cost estimation and/or tracking of intra-scan focal-spot displacement), that are not abstract and that cannot be performed as a set of mental acts by a human. Further, some of the processes performed can be performed by a specialized computer (e.g., X-ray tube, gantry, multi-channel-multi-row detector) for carrying out defined tasks related to low-cost estimation/tracking of intra-scan focal-spot displacement. For example, such defined tasks can include: causing, by a device operatively coupled to a processor, a medical imaging scanner to perform an air scan, wherein the medical imaging scanner has an X-ray tube, a gantry, and a multi-channel-multi-row detector; accessing, by the device, data produced by the medical imaging scanner and relating to the air scan, wherein the data includes a set of gantry angles swept by the X-ray tube during the air scan, wherein the data includes a set of intensity value matrices recorded by the multi-channel-multi-row detector during the air scan, and wherein the set of intensity value matrices respectively correspond to the set of gantry angles; computing, by the device, a set of channel-spanning intensity slopes based on the set of intensity value matrices, wherein the set of channel-spanning intensity slopes respectively correspond to the set of gantry angles; applying, by the device, a slope-to-displacement transfer function to the set of channel-spanning intensity slopes, thereby yielding a set of focal-spot displacements that respectively correspond to the set of gantry angles; and/or initiating, by the device, one or more electronic actions based on the set of focal-spot displacements. In various cases, such one or more electronic actions can include plotting, by the device and on an electronic display, the set of focal-spot displacements against the set of gantry angles.

Such defined tasks are not performed manually by humans. Indeed, neither the human mind nor a human with pen and paper can electronically cause a medical scanner (e.g., CT scanner) to perform an air scan, can electronically access Hounsfield matrices recorded by a multi-channelmulti-row detector of such medical scanner, can electronically compute slope values based on such Hounsfield matrices, and/or can electronically apply a slope-to-displacement transfer function to such slope values, thereby yielding a set of intra-scan focal-spot displacements. Instead, various embodiments described herein are inherently and inextricably tied to computer technology and cannot be implemented outside of a computing environment (e.g., a medical imaging scanner is an inherently-computerized device that can generate medical images by passing X-ray radiation through an object of interest, such as an anatomical structure of a patient; a computerized tool that can estimate and/or track the position of the focal-spot of such a medical imaging scanner based on air scan data produced by the medical imaging scanner and without having to perform a tungsten edge measurement at every possible gantry angle is likewise inherently-computerized and cannot be implemented in any sensible, practical, or reasonable way without computers).

Moreover, various embodiments can integrate into a practical application various teachings described herein relating to low-cost estimation and/or tracking of intra-scan focal-spot displacement. As explained above, one potential way to measure/track intra-scan focal-spot displacement would be to perform a tungsten edge measurement (e.g., a partial edge scan) at every possible gantry angle of a medical imaging scanner. However, this would be highly burdensome and time-consuming. To address this problem, the present inventors devised various techniques for estimating/tracking intra-scan focal-spot displacement that utilize channel-spanning slope. More specifically, the medical imaging scanner can perform an air scan, which can involve sweeping an X-ray tube of the medical imaging scanner through a set of gantry angles, and recording by a multi-channel-multi-row detector of the medical imaging scanner an intensity value matrix at each gantry angle. Row-averaging can then be performed on each intensity value matrix, thereby yielding a set of row-averaged intensity value vectors. Next, a set of channel-spanning slopes can be generated by fitting linear trendlines to each of the row-averaged intensity value vectors. Finally, a slope-to-displacement transfer function can be applied to the set of channel-spanning slopes, thereby yielding a set of focal-spot displacements that respectively correspond to the set of gantry angles. In various cases, the set of focal-spot displacements can be considered as representing how and/or where the focal-spot of the medical imaging scanner moves as the X-ray tube rotates about/along the gantry. That is, the set of focal-spot displacements can be considered as indicating/representing the intra-scan motion of the focal-spot. Although such a technique does involve computing a channel-spanning slope for each gantry angle, such computation can be much less burdensome and/or time-consuming than performing a tungsten edge scan at each gantry angle. Furthermore, although the slope-to-displacement transfer function can be obtained experimentally by utilizing tungsten edge measurements, it can take orders of magnitude fewer tungsten edge measurements to accurately identify the slope-to-displacement transfer function than it would take to perform a separate tungsten edge measurement at every gantry angle. Therefore, in any case, various embodiments described herein can allow for the estimation and/or tracking of intra-scan focal-spot displacements in a significantly less costly manner than would be possible if a separate tungsten edge measurement were performed for every gantry angle. A computerized tool that can estimate/track intra-scan focal-spot displacement in such a low-cost fashion certainly constitutes a concrete and tangible technical improvement in the field of focal-spots of medical imaging scanners, and thus surely qualifies as a useful and practical application of computers.

Furthermore, it must be emphasized that various embodiments described herein are not merely directed to mathematical computations without significantly more. Indeed, as described herein, the present inventors devised an efficient, low-cost technique to estimate/track intra-scan focal-spot motion. Rather than performing a tungsten edge measurement at every possible gantry angle, such efficient, low-cost technique can involve computing a channel-spanning intensity slope at each gantry angle and applying a slope-to-displacement transfer function to such channel-spanning intensity slopes. Please note that the specific details for enabling/describing such functionality are presented herein as a series of steps, actions, and/or mathematical computations/calculations performed by a computer processor, because there is simply no other way to intelligently discuss the subject innovation. Notwithstanding that the subject innovation utilizes and/or involves such mathematical computations/calculations, the subject innovation is nevertheless a practical, technical solution to a real-world, technical problem. After all, and as explained herein, estimating/tracking intra-scan focal-spot motion via the computation of channel-spanning slopes is a novel technique that is much less burdensome in terms of time, effort, and resources as compared to performing a separate tungsten edge measurement at each gantry angle. The fact that the subject innovation involves mathematical concepts does not nullify or override such technical benefit.

Further still, various embodiments described herein can control real-world tangible devices based on the disclosed teachings. For example, various embodiments described herein can electronically control (e.g., power up, power down, calibrate, engage, disengage) real-world medical imaging scanners (e.g., CT scanners) that have real-world X-ray tubes, real-world gantries, and/or real-world multi-channel-multi-row detectors.

It should be appreciated that the herein figures and description provide non-limiting examples and are not necessarily drawn to scale.

FIG. 1 illustrates a block diagram of an example, non-limiting system 100 that can facilitate low-cost estimation and/or tracking of intra-scan focal-spot displacement in accordance with one or more embodiments described herein. As shown, an intra-scan focal-spot tracking system 102 can be electronically integrated, via any suitable wired and/or wireless electronic connections, with a medical scanner 104.

In various embodiments, the medical scanner 104 can be any suitable medical imaging device as desired. For example, the medical scanner 104 can, in various aspects, be a CT scanner. In any case, the medical scanner 104 can include an X-ray tube 106, a gantry 108, and/or a detector 110. In various aspects, the X-ray tube 106 can rotate to different angular positions about and/or along the gantry 108. In various instances, the detector 110 can also rotate about/along the gantry 108, so as to maintain angular opposition to the X-ray tube 106 (e.g., the angular position of the detector 110 can be 180 degrees different from that of the X-ray tube 106). Moreover, in various instances, the X-ray tube 106 can include a cathode (not shown) and an anode (not shown), where a voltage applied to such cathode and anode can cause an electron beam to be accelerated from the cathode to the anode. When the electron beam strikes the anode, X-ray radiation can be produced and can radiate and/or propagate toward a central bore of the gantry 108. When an object (e.g., an anatomical structure of a medical patient) is placed within the central bore of the gantry 108, the X-ray radiation can pass through the object and can be recorded by the detector 110, thereby yielding medical images (e.g., CT images). This is shown with respect to FIG. 2.

Figure 2:
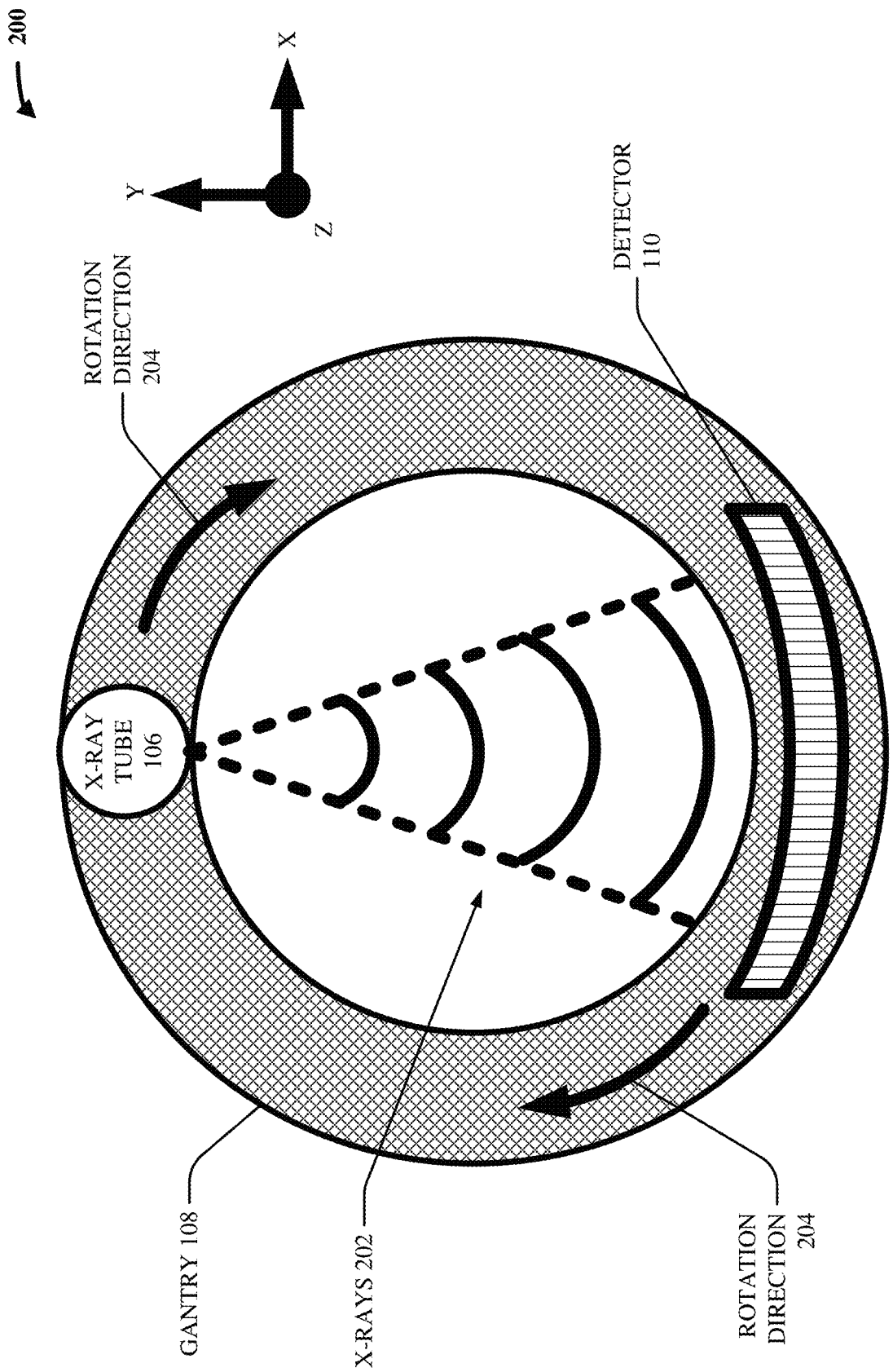
FIG. 2 illustrates an example, non-limiting block diagram of a medical scanner in accordance with one or more embodiments described herein.

FIG. 2 illustrates an example, non-limiting block diagram 200 of a medical scanner in accordance with one or more embodiments described herein. In other words, FIG. 2 shows a non-limiting example embodiment of the medical scanner 104. As shown, the gantry 108 can be a circular path and/or ring about which and/or along which both the X-ray tube 106 and the detector 110 can controllably rotate. As a non-limiting example, the X-ray tube 106 can emit one or more X-rays 202 radially toward a central bore of the gantry 108, and the X-ray tube 106 can change the direction of emission of the X-rays 202 by moving about/along the gantry 108 in a rotation direction 204. Furthermore, the detector 110 can also rotate in the rotation direction 204 so as to maintain angular opposition to the X-ray tube 106, thereby allowing the detector 110 to capture and/or record the X-rays 202.

Although not explicitly shown in FIG. 2, those having ordinary skill in the art will appreciate that the detector 110 can exhibit any suitable architecture as desired. For example, the detector 110 can, in some cases, exhibit a multi-channel and/or multi-row architecture. In such case, the detector 110 can have any suitable number of detector channels that are positioned along a circumferential direction of the gantry 108 (e.g., in the x-y plane of FIG. 2), and the detector 110 can have any suitable number of detector rows that are positioned along a longitudinal/bore direction of the gantry 108 (e.g., along the z-axis of FIG. 2).

As those having ordinary skill in the art will further appreciate, the location and/or position of the X-ray tube 106 along the gantry 108 can be described by a gantry angle (e.g., measured in degrees and/or radians), where the sign of the gantry angle can indicate a direction (e.g., counterclockwise and/or clockwise) in which the X-ray tube 106 has rotated about/along the gantry 108 from a reference position, and/or where the magnitude of the gantry angle can indicate how far the X-ray tube 106 has rotated about/along the gantry 108 from the reference position.

In any case, the focal-spot of the medical scanner 104 can shift, drift, and/or otherwise move as the X-ray tube 106 rotates about/along the gantry 108. As mentioned above, such motion, which can be referred to as intra-scan focal-spot displacement, can be caused by gravity and/or the Earth's magnetic field interacting differently with the X-ray tube 106 at different gantry angles. Unfortunately, such intra-scan focal-spot displacement can cause significant imaging artefacts (e.g., noticeable image streaks, noticeable image shadows, band, ring) to be recorded by the detector 110. Correction and/or reduction of such imaging artefacts can depend upon estimating, tracking, and/or otherwise measuring how the position of the focal-spot changes as the X-ray tube 106 rotates about/along the gantry 108. As described herein, the intra-scan focal-spot tracking system 102 can facilitate such estimating, tracking, and/or measuring in low-cost and/or low-burden fashion.

Referring back to FIG. 1, in various embodiments, the intra-scan focal-spot tracking system 102 can comprise a processor 112 (e.g., computer processing unit, microprocessor) and a computer-readable memory 114 that is operably and/or operatively and/or communicatively connected/coupled to the processor 112. The computer-readable memory 114 can store computer-executable instructions which, upon execution by the processor 112, can cause the processor 112 and/or other components of the intra-scan focal-spot tracking system 102 (e.g., scan component 116, receiver component 118, average component 120, slope component 122, displacement component 124, and/or execution component 126) to perform one or more acts. In various embodiments, the computer-readable memory 114 can store computer-executable components (e.g., scan component 116, receiver component 118, average component 120, slope component 122, displacement component 124, and/or execution component 126), and the processor 112 can execute the computer-executable components.

In various embodiments, the intra-scan focal-spot tracking system 102 can comprise a scan component 116. In various aspects, as described herein, the scan component 116 can electronically instruct, command, and/or otherwise cause the medical scanner 104 to perform an air scan.

In various embodiments, the intra-scan focal-spot tracking system 102 can further comprise a receiver component 118. In various instances, as described herein, the receiver component 118 can electronically receive, retrieve, and/or access data produced during and/or in response to the air scan by the medical scanner 104. In various cases, the data can include a set of gantry angles swept by the X-ray tube 106 during the air scan, and/or the data can further include a set of intensity value matrices recorded by the detector 110 and that respectively correspond to the set of gantry angles.

In various embodiments, the intra-scan focal-spot tracking system 102 can further comprise an average component 120. In various aspects, as described herein, the average component 120 can electronically perform row-averaging on the set of intensity value matrices, thereby yielding a set of row-averaged intensity value vectors.

In various embodiments, the intra-scan focal-spot tracking system 102 can further comprise a slope component 122. In various instances, as described herein, the slope component 122 can electronically compute a set of channel-spanning intensity slopes based on the set of row-averaged intensity value vectors.

In various embodiments, the intra-scan focal-spot tracking system 102 can further comprise a displacement component 124. In various aspects, as described herein, the displacement component 124 can electronically compute, via a slope-to-displacement transfer function, a set of focal-spot displacements based on the set of channel-spanning intensity slopes.

In various embodiments, the intra-scan focal-spot tracking system 102 can further comprise an execution component 126. In various instances, as described herein, the execution component 126 can electronically perform one or more electronic actions based on the set of focal-spot displacements (e.g., plotting the set of focal-spot displacements against the set of gantry angles, making an electronic recommendation by comparing the set of focal-spot displacements to a threshold value).

Figure 3:
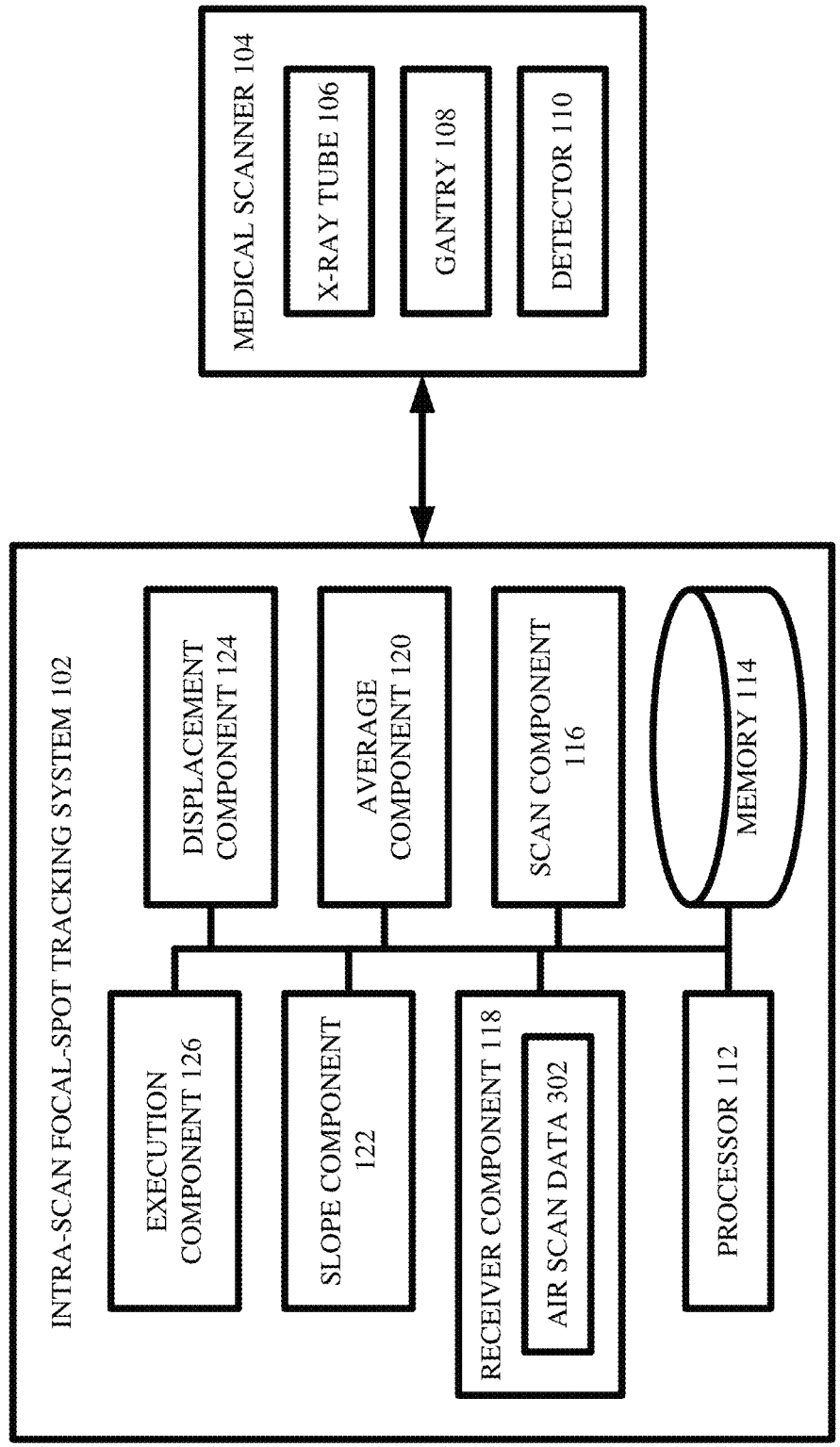
FIG. 3 illustrates a block diagram of an example, non-limiting system including air scan data that facilitates low-cost estimation and/or tracking of intra-scan focal-spot displacement in accordance with one or more embodiments described herein.

FIG. 3 illustrates a block diagram of an example, non-limiting system 300 including air scan data that can facilitate low-cost estimation and/or tracking of intra-scan focal-spot displacement in accordance with one or more embodiments described herein. As shown, the system 300 can, in some cases, comprise the same components as the system 100, and can further comprise air scan data 302.

In various embodiments, the scan component 116 can electronically instruct, electronically command, and/or otherwise electronically cause the medical scanner 104 to perform an air scan. That is, with only air in the bore of the gantry 108, the X-ray tube 106 can sweep through any suitable set of gantry angles. At each gantry angle, the X-ray tube 106 can emit X-rays radially through the bore of the gantry 108, and the detector 110 can capture/record such X-rays. In various cases, electronic data produced by the medical scanner 104 during, in response to, and/or otherwise because of such air scan can be considered as the air scan data 302.

In various embodiments, the receiver component 118 can electronically receive and/or otherwise electronically access the air scan data 302. In various instances, the receiver component 118 can electronically retrieve the air scan data 302 from any suitable centralized and/or decentralized data structure (not shown). In various other instances, the receiver component 118 can electronically retrieve the air scan data 302 from the medical scanner 104 itself. In any case, the receiver component 118 can electronically obtain and/or access the air scan data 302, such that other components of the intra-scan focal-spot tracking system 102 can electronically interact with the air scan data 302.

In various aspects, the air scan data 302 can be any suitable electronic data structure that includes/represents a set of gantry angles swept by the X-ray tube 106 during the air scan and/or that includes/represents a set of intensity value matrices recorded by the detector 110 during the air scan. This is further explained with respect to FIGS. 4-5.

Figure 4:
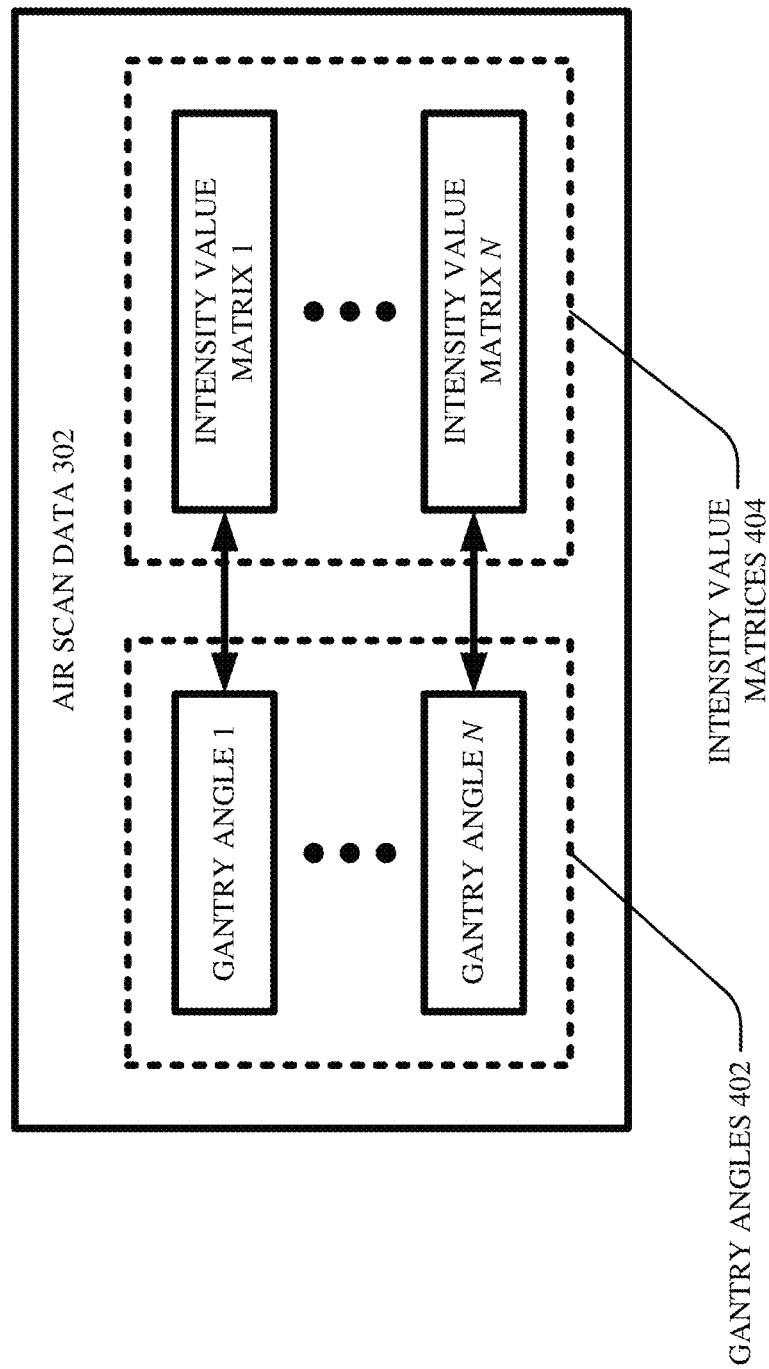
FIG. 4 illustrates an example, non-limiting block diagram showing air scan data including a set of gantry angles and/or a set of intensity value matrices in accordance with one or more embodiments described herein.

FIG. 4 illustrates an example, non-limiting block diagram 400 showing air scan data including a set of gantry angles and/or a set of intensity value matrices in accordance with one or more embodiments described herein. That is, FIG. 4 depicts a non-limiting example embodiment of the air scan data 302. As shown, the air scan data 302 can indicate and/or include a set of gantry angles 402 and/or a set of intensity value matrices 404 that respectively correspond to the set of gantry angles 402.

In various aspects, the set of gantry angles 402 can be the set of gantry angles (e.g., can be the angular interval) that the X-ray tube 106 sweeps about/along the gantry 108 during the air scan. In various instances, the set of gantry angles 402 can include n angle values (e.g., measured in degrees and/or radians) for any suitable positive integer n: a gantry angle 1 to a gantry angle n. For example, the gantry angle 1 can be considered as a scalar that represents a first position about/along the gantry 108 and to which the X-ray tube 106 rotates during the air scan, and the gantry angle n can be considered as a scalar that represents an n-th position about/along the gantry 108 and to which the X-ray tube 106 rotates during the air scan.

In various aspects, the set of intensity value matrices 404 can represent the electronic output of the detector 110 during and/or in response to the air scan. In various instances, the set of intensity value matrices 404 can respectively correspond (e.g., in one-to-one fashion) with the set of gantry angles 402. Accordingly, in various cases, the set of intensity value matrices 404 can include n matrices: an intensity value matrix 1 to an intensity value matrix n. More specifically, the intensity value matrix 1 can be considered as the output of the detector 110 when the X-ray tube 106 emits X-rays from the gantry angle 1 during the air scan. Similarly, the intensity value matrix n can be considered as the output of the detector 110 when the X-ray tube 106 emits X-rays from the gantry angle n during the air scan. As those having ordinary skill in the art will appreciate, the dimensionality and/or format of each intensity value matrix can depend upon the architecture of the detector 110. This is further described with respect to FIG. 5.

Figure 5:
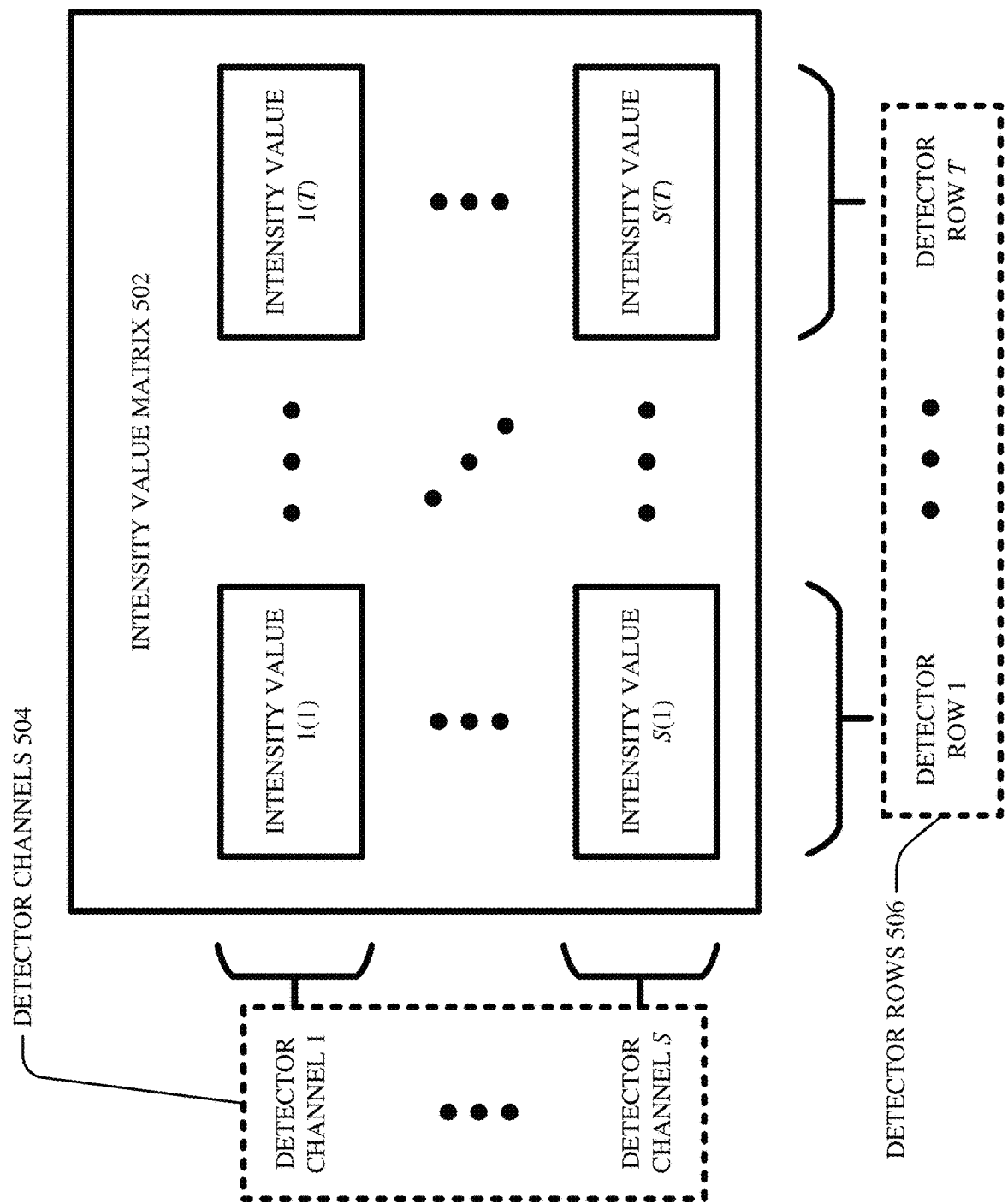
FIG. 5 illustrates an example, non-limiting block diagram showing an intensity value matrix in accordance with one or more embodiments described herein.

FIG. 5 illustrates an example, non-limiting block diagram 500 showing an intensity value matrix in accordance with one or more embodiments described herein. That is, FIG. 5 depicts an example, non-limiting embodiment of any one of the set of intensity value matrices 404.

In various embodiments, there can be an intensity value matrix 502. In various aspects, the intensity value matrix 502 can be any one of the set of intensity value matrices 404. In various instances, the detector 110 can have s detector channels for any suitable positive integer s: a detector channel 1 to a detector channel s. In various cases, the detector channel 1 to the detector channel s can be considered as collectively forming a set of detector channels 504. In various aspects, the detector 110 can have t detector rows for any suitable positive integer t: a detector row 1 to a detector row t. In various instances, the detector row 1 to the detector row t can be considered as collectively forming the set of detector rows 506. Because the detector 110 can have s channels and t rows, the intensity value matrix 502 can, as shown, be an s-by-t matrix, with each element of such s-by-t matrix respectively corresponding to a specific channel and a specific row of the detector 110. For example, an intensity value 1(1) of the intensity value matrix 502 can be a scalar Hounsfield unit value that is/was measured, captured, and/or otherwise recorded by the detector channel 1 and the detector row 1 of the detector 110, when the X-ray tube 106 was positioned at a particular gantry angle in the set of gantry angles 402. As another example, an intensity value 1(t) of the intensity value matrix 502 can be a scalar Hounsfield unit value that is/was measured, captured, and/or otherwise recorded by the detector channel 1 and the detector row t of the detector 110, when the X-ray tube 106 was positioned at the particular gantry angle. As still another example, an intensity value s(1) of the intensity value matrix 502 can be a scalar Hounsfield unit value that is/was measured, captured, and/or otherwise recorded by the detector channel s and the detector row 1 of the detector 110, when the X-ray tube 106 was positioned at the particular gantry angle. As yet another example, an intensity value s(t) of the intensity value matrix 502 can be a scalar Hounsfield unit value that is/was measured, captured, and/or otherwise recorded by the detector channel s and the detector row t of the detector 110, when the X-ray tube 106 was positioned at the particular gantry angle.

Figure 6:
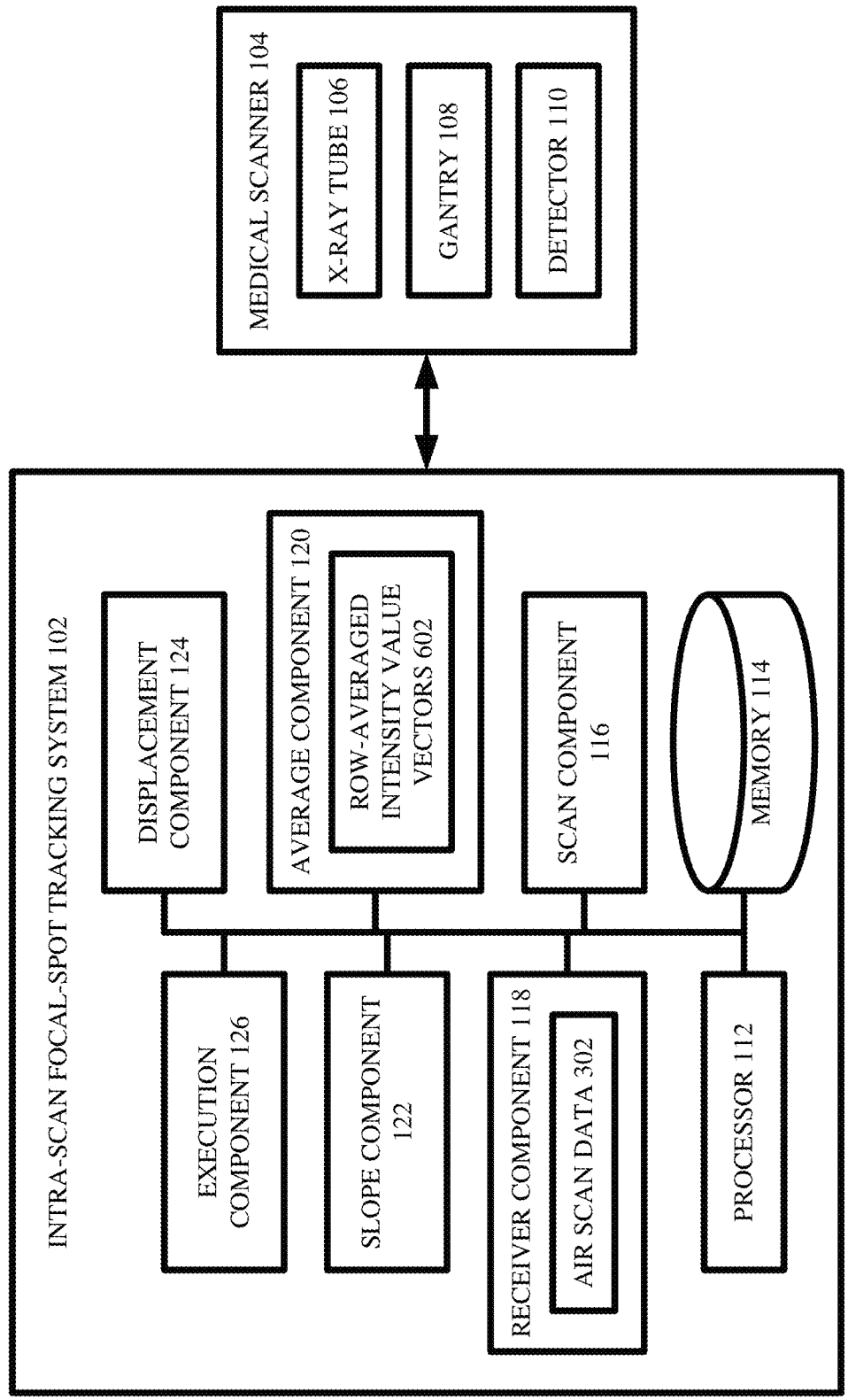
FIG. 6 illustrates a block diagram of an example, non-limiting system including a set of row-averaged intensity value vectors that facilitates low-cost estimation and/or tracking of intra-scan focal-spot displacement in accordance with one or more embodiments described herein.

FIG. 6 illustrates a block diagram of an example, non-limiting system 600 including a set of row-averaged intensity value vectors that can facilitate low-cost estimation and/or tracking of intra-scan focal-spot displacement in accordance with one or more embodiments described herein. As shown, the system 600 can, in some cases, comprise the same components as the system 300, and can further comprise a set of row-averaged intensity value vectors 602.

In various embodiments, the average component 120 can electronically generate, electronically calculate, and/or otherwise electronically compute the set of row-averaged intensity value vectors 602, based on the air scan data 302. This is explained more with respect to FIGS. 7-8.

Figure 7:
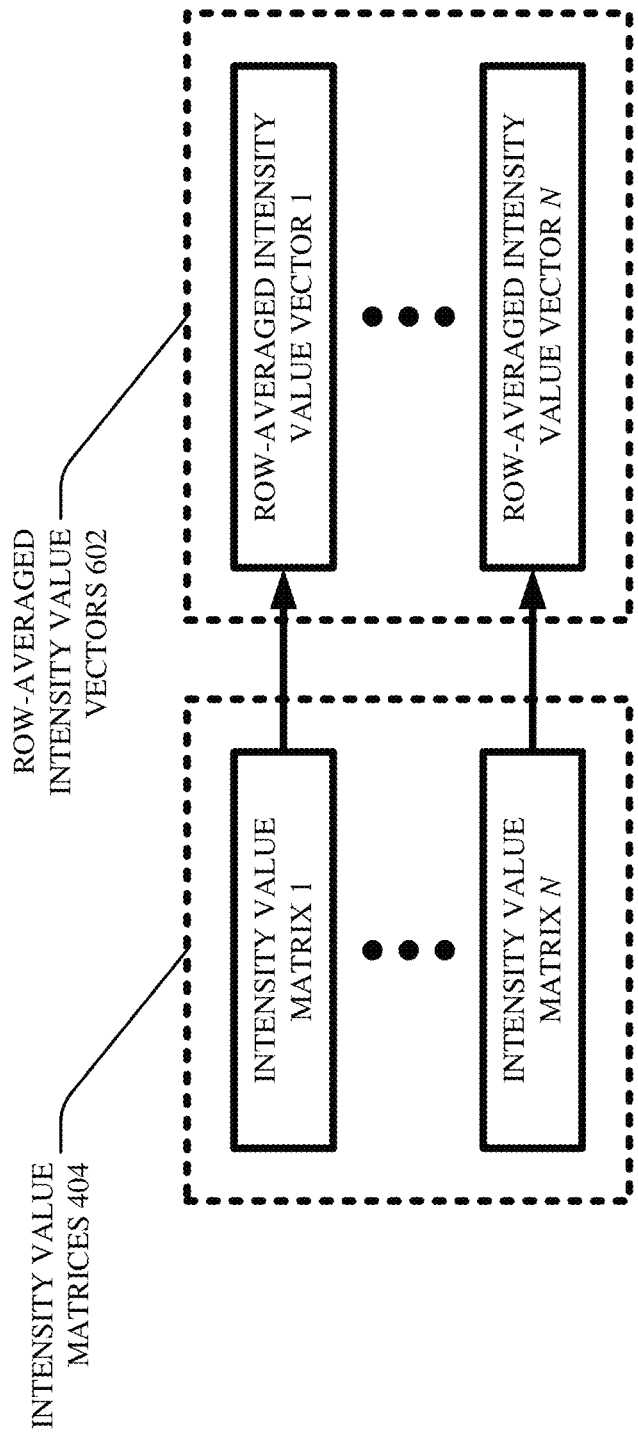
FIG. 7 illustrates an example, non-limiting block diagram showing a set of row-averaged intensity value vectors in accordance with one or more embodiments described herein.

FIG. 7 illustrates an example, non-limiting block diagram 700 showing a set of row-averaged intensity value vectors in accordance with one or more embodiments described herein. That is, FIG. 7 depicts a non-limiting example embodiment of the set of row-averaged intensity value vectors 602.

As shown, the set of row-averaged intensity value vectors 602 can correspond (e.g., in one-to-one fashion) with the set of intensity value matrices 404. Accordingly, because the set of intensity value matrices 404 can include n matrices, the set of row-averaged intensity value vectors 602 can include n vectors: a row-averaged intensity value vector 1 to a row-averaged intensity value vector n. In other words, there can be one row-averaged intensity value vector per intensity value matrix. For example, the row-averaged intensity value vector 1 can correspond to the intensity value matrix 1. That is, the average component 120 can electronically compute the row-averaged intensity value vector 1 based on (e.g., by mathematically manipulating) the intensity value matrix 1. Moreover, because the row-averaged intensity value vector 1 can correspond to the intensity value matrix 1, and because the intensity value matrix 1 can correspond to the gantry angle 1, the row-averaged intensity value vector 1 can be considered as corresponding to the gantry angle 1. Likewise, as another example, the row-averaged intensity value vector n can correspond to the intensity value matrix n. Again, this can mean that the average component 120 can electronically compute the row-averaged intensity value vector n based on (e.g., by mathematically manipulating) the intensity value matrix n. Further, because the row-averaged intensity value vector n can correspond to the intensity value matrix n, and because the intensity value matrix n can correspond to the gantry angle n, the row-averaged intensity value vector n can be considered as corresponding to the gantry angle n. In various instances, each of the set of row-averaged intensity value vectors 602 can be computed by performing row-averaging on a respectively corresponding one of the set of intensity value matrices 404. This is explained more with respect to FIG. 8.

Figure 8:
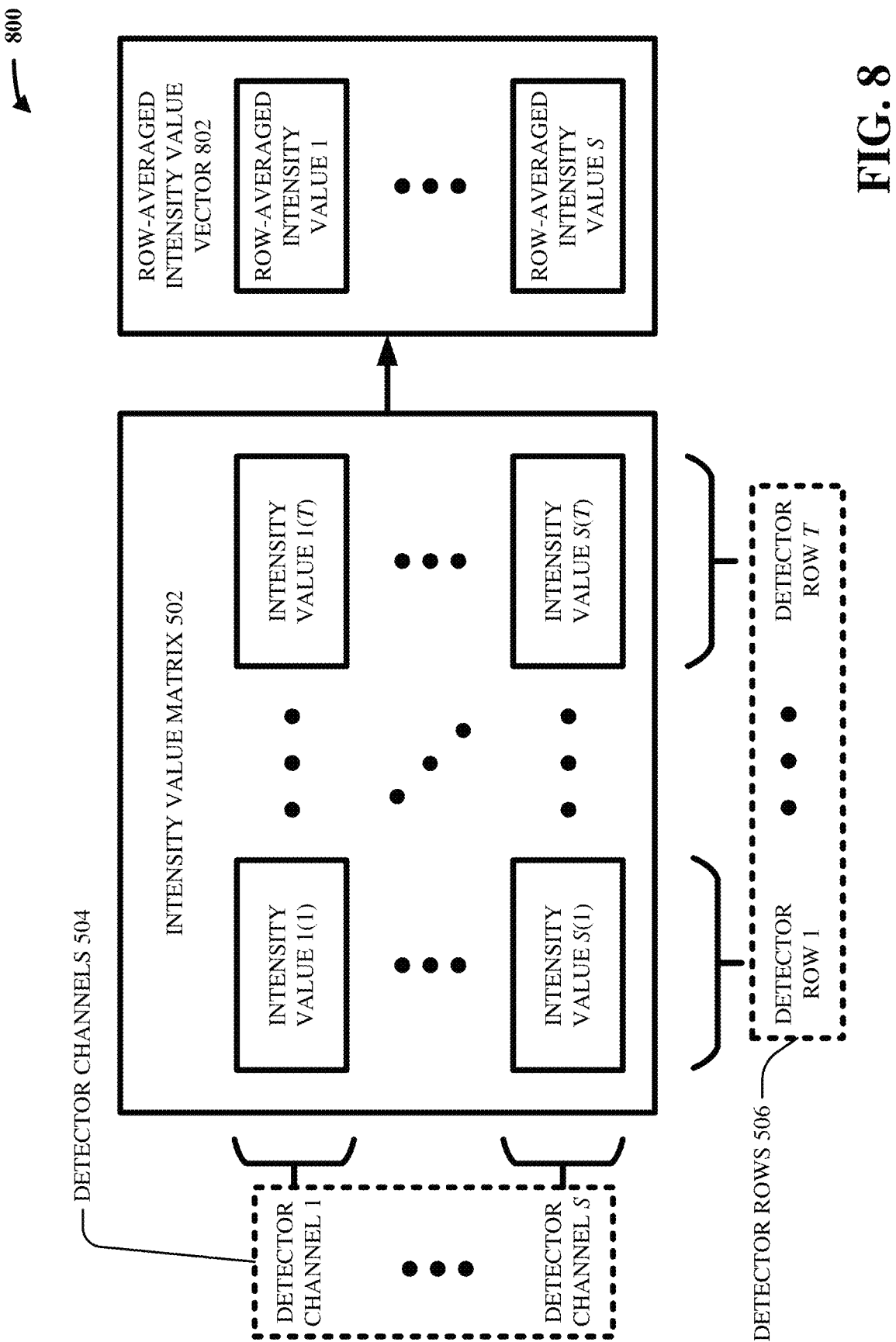
FIG. 8 illustrates an example, non-limiting block diagram showing how a row-averaged intensity value vector can be generated from an intensity value matrix in accordance with one or more embodiments described herein.

FIG. 8 illustrates an example, non-limiting block diagram 800 showing how a row-averaged intensity value vector can be generated from an intensity value matrix in accordance with one or more embodiments described herein.

In various aspects, the intensity value matrix 502 can be as mentioned above. In various instances, the average component 120 can electronically generate a row-averaged intensity value vector 802 based on the intensity value matrix 502. In other words, the intensity value matrix 502 can be any one of the set of intensity value matrices 404, and the row-averaged intensity value vector 802 can be the one of the set of row-averaged intensity value vectors 602 that corresponds to the intensity value matrix 502. In various cases, the average component 120 can generate the row-averaged intensity value vector 802 by performing row-averaging on the intensity value matrix 502. More specifically, because the detector 110 can have s channels and t rows, the intensity value matrix 502 can be an s-by-t matrix of Hounsfield unit values, as mentioned above, and the row-averaged intensity value vector 802 can be an s-element vector of averaged Hounsfield unit values. That is, the row-averaged intensity value vector 802 can have s elements: a row-averaged intensity value 1 to a row-averaged intensity value s. In various aspects, the row-averaged intensity value 1 can be the average (e.g., the mean) of all the Hounsfield unit values in the intensity value matrix 502 that are associated with the detector channel 1. In other words, the row-averaged intensity value 1 can be equal to (and/or otherwise based on) the average (e.g., the mean) of the intensity value 1(1) to the intensity value 1(t). Similarly, in various instances, the row-averaged intensity value s can be the average (e.g., the mean) of all the Hounsfield unit values in the intensity value matrix 502 that are associated with the detector channel s. In other words, the row-averaged intensity value s can be equal to (and/or otherwise based on) the average (e.g., the mean) of the intensity value s(1) to the intensity value s(t). Therefore, in various cases, the row-averaged intensity value vector 802 can be considered as the result obtained by averaging out the set of detector rows 506 from the intensity value matrix 502.

In any case, the average component 120 can generate the set of row-averaged intensity value vectors 602 based on the air scan data 302.

Figure 9:
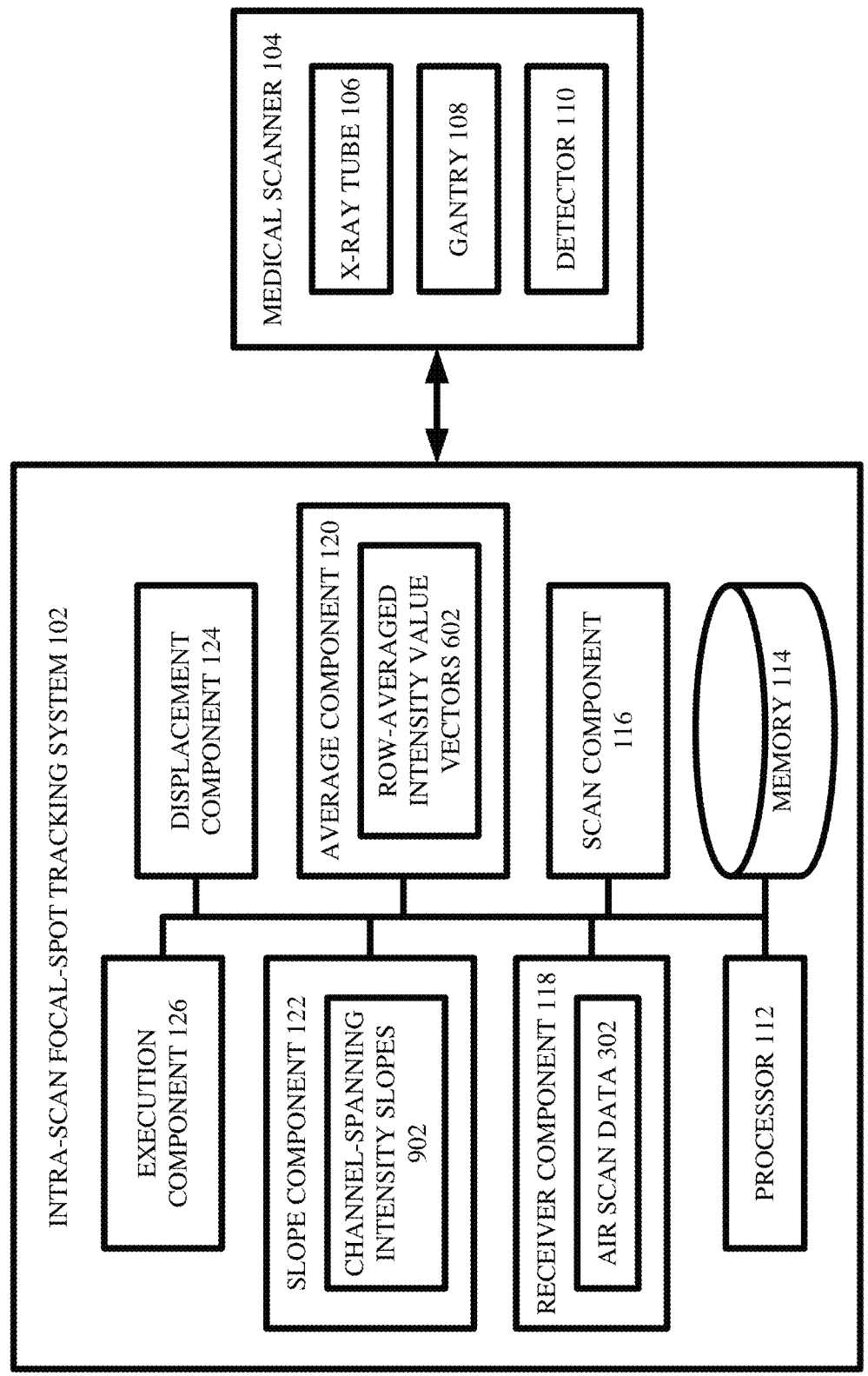
FIG. 9 illustrates a block diagram of an example, non-limiting system including a set of channel-spanning intensity slopes that facilitates low-cost estimation and/or tracking of intra-scan focal-spot displacement in accordance with one or more embodiments described herein.

FIG. 9 illustrates a block diagram of an example, non-limiting system 900 including a set of channel-spanning intensity slopes that can facilitate low-cost estimation and/or tracking of intra-scan focal-spot displacement in accordance with one or more embodiments described herein. As shown, the system 900 can, in some cases, comprise the same components as the system 600, and can further comprise a set of channel-spanning intensity slopes 902.

In various embodiments, the slope component 122 can electronically generate, electronically calculate, and/or otherwise electronically compute the set of channel-spanning intensity slopes 902 based on the set of row-averaged intensity value vectors 602. This is explained more with respect to FIGS. 10-11.

Figure 10:
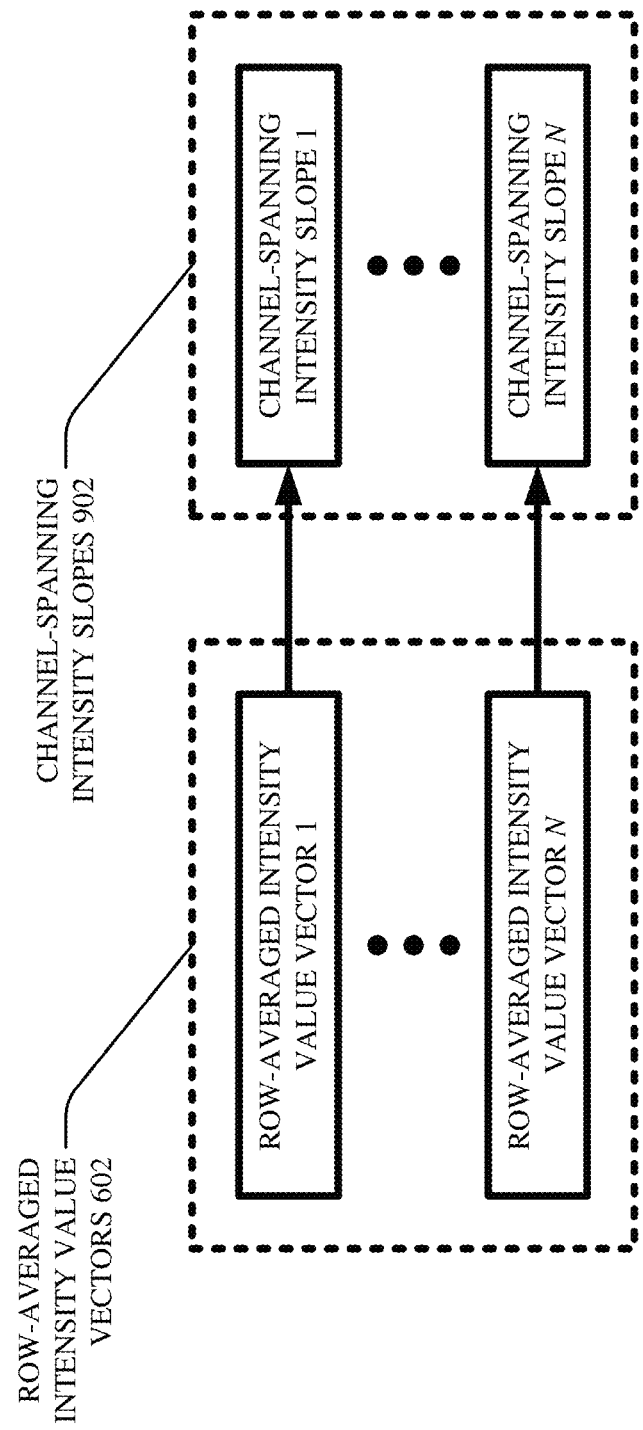
FIG. 10 illustrates an example, non-limiting block diagram showing a set of channel-spanning intensity slopes in accordance with one or more embodiments described herein.

FIG. 10 illustrates an example, non-limiting block diagram showing a set of channel-spanning intensity slopes in accordance with one or more embodiments described herein. That is, FIG. 10 depicts a non-limiting example embodiment of the set of channel-spanning intensity slopes 902.

As shown, the set of channel-spanning intensity slopes 902 can correspond (e.g., in one-to-one fashion) with the set of row-averaged intensity value vectors 602. Accordingly, because the set of row-averaged intensity value vectors 602 can include n vectors, the set of channel-spanning intensity slopes 902 can include n slopes: a channel-spanning intensity slope 1 to a channel-spanning intensity slope n. In other words, there can be one channel-spanning intensity slope per row-averaged intensity value vector. For example, the channel-spanning intensity slope 1 can correspond to the row-averaged intensity value vector 1. That is, the slope component 122 can electronically compute the channel-spanning intensity slope 1 based on (e.g., by mathematically manipulating) the row-averaged intensity value vector 1. Moreover, because the channel-spanning intensity slope 1 can correspond to the row-averaged intensity value vector 1, and because the row-averaged intensity value vector 1 can correspond to the gantry angle 1, the channel-spanning intensity slope 1 can be considered as corresponding to the gantry angle 1. Likewise, as another example, the channel-spanning intensity slope n can correspond to the row-averaged intensity value vector n. Again, this can mean that the slope component 122 can electronically compute the channel-spanning intensity slope n based on (e.g., by mathematically manipulating) the row-averaged intensity value vector n. Further, because the channel-spanning intensity slope n can correspond to the row-averaged intensity value vector n, and because the row-averaged intensity value vector n can correspond to the gantry angle n, the channel-spanning intensity slope n can be considered as corresponding to the gantry angle n. In various instances, each of the set of channel-spanning intensity slopes 902 can be computed by fitting a linear trendline to a respectively corresponding one of the set of row-averaged intensity value vectors 602. This is explained more with respect to FIG. 11.

Figure 11:
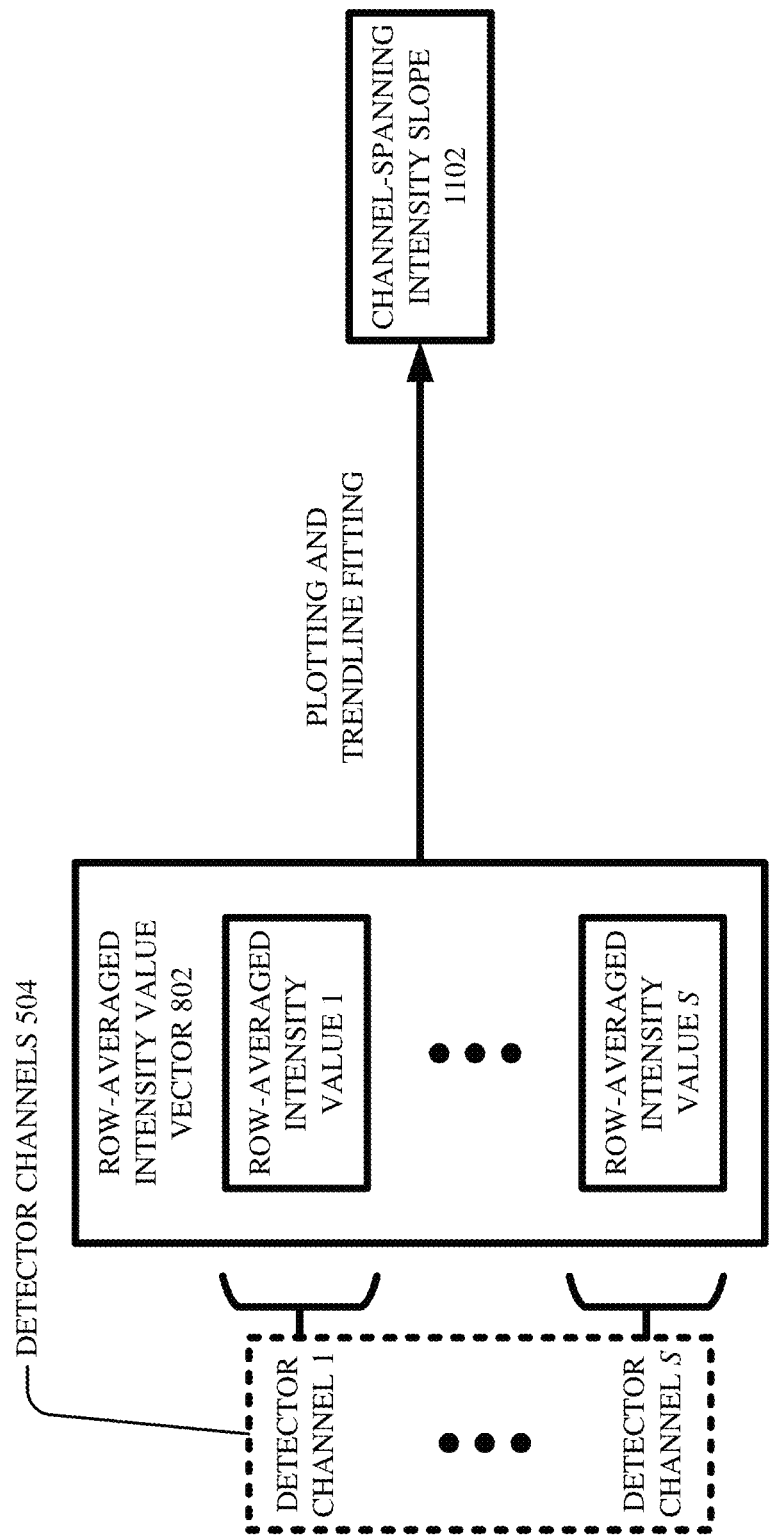
FIG. 11 illustrates an example, non-limiting block diagram showing how a channel-spanning intensity slope can be generated from a row-averaged intensity value vector in accordance with one or more embodiments described herein.

FIG. 11 illustrates an example, non-limiting block diagram 1100 showing how a channel-spanning intensity slope can be generated from a row-averaged intensity value vector in accordance with one or more embodiments described herein.

In various aspects, the row-averaged intensity value vector 802 can be as mentioned above. In various instances, the slope component 122 can electronically generate a channel-spanning intensity slope 1102 based on the row-averaged intensity value vector 802. In other words, the row-averaged intensity value vector 802 can be any one of the set of row-averaged intensity value vectors 602, and the channel-spanning intensity slope 1102 can be the one of the set of channel-spanning intensity slopes 902 that corresponds to the row-averaged intensity value vector 802. In various cases, the channel-spanning intensity slope 1102 can be a scalar that is equal to (and/or otherwise based on) the slope of a linear trendline that is fitted to the row-averaged intensity value vector 802.

In particular, in various aspects, the slope component 122 can select any suitable contiguous interval of channels from the set of detector channels 504. In some cases, the slope component 122 can select as the contiguous interval the entire set of detector channels 504 (e.g., can select the interval from the detector channel 1 to the detector channel s). In other cases, the slope component 122 can select as the contiguous interval less than the entire set of detector channels 504 (e.g., can select the interval from the detector channel u to the detector channel v, for any suitable integers u and v where 1≤u<v≤s). In any case, because the row-averaged intensity value vector 802 can have one element (e.g., one intensity value) per detector channel, the selection of the contiguous interval of channels from the set of detector channels 504 can be considered as analogous and/or equivalent to a selection of a corresponding contiguous interval of elements from the row-averaged intensity value vector 802. For example, the selection of the contiguous interval of channels that starts with the detector channel u and that ends with the detector channel v can be considered as corresponding to a contiguous interval of elements of the row-averaged intensity value vector 802 that starts with a row-averaged intensity value u and that ends with a row-averaged intensity value v. In various aspects, the slope component 122 can plot such contiguous interval of elements of the row-averaged intensity value vector 802. In various instances, the slope component 122 can fit via any suitable technique (e.g., least sum of squares) a linear trendline and/or a line of best fit to such plot. In various cases, the slope of such linear trendline and/or line of best fit can be considered as the channel-spanning intensity slope 1102.

Although a contiguous interval of channels and/or elements of the row-averaged intensity value vector 802 is described herein, this is a mere non-limiting example for ease of explanation. Those having ordinary skill in the art will appreciate that, in various cases, a non-contiguous interval of channels and/or elements of the row-averaged intensity value vector 802 can be plotted and/or fitted to generate the channel-spanning intensity slope 1102.

In any case, the slope component 122 can generate the set of channel-spanning intensity slopes 902 based on the set of row-averaged intensity value vectors 602.

Figure 12:
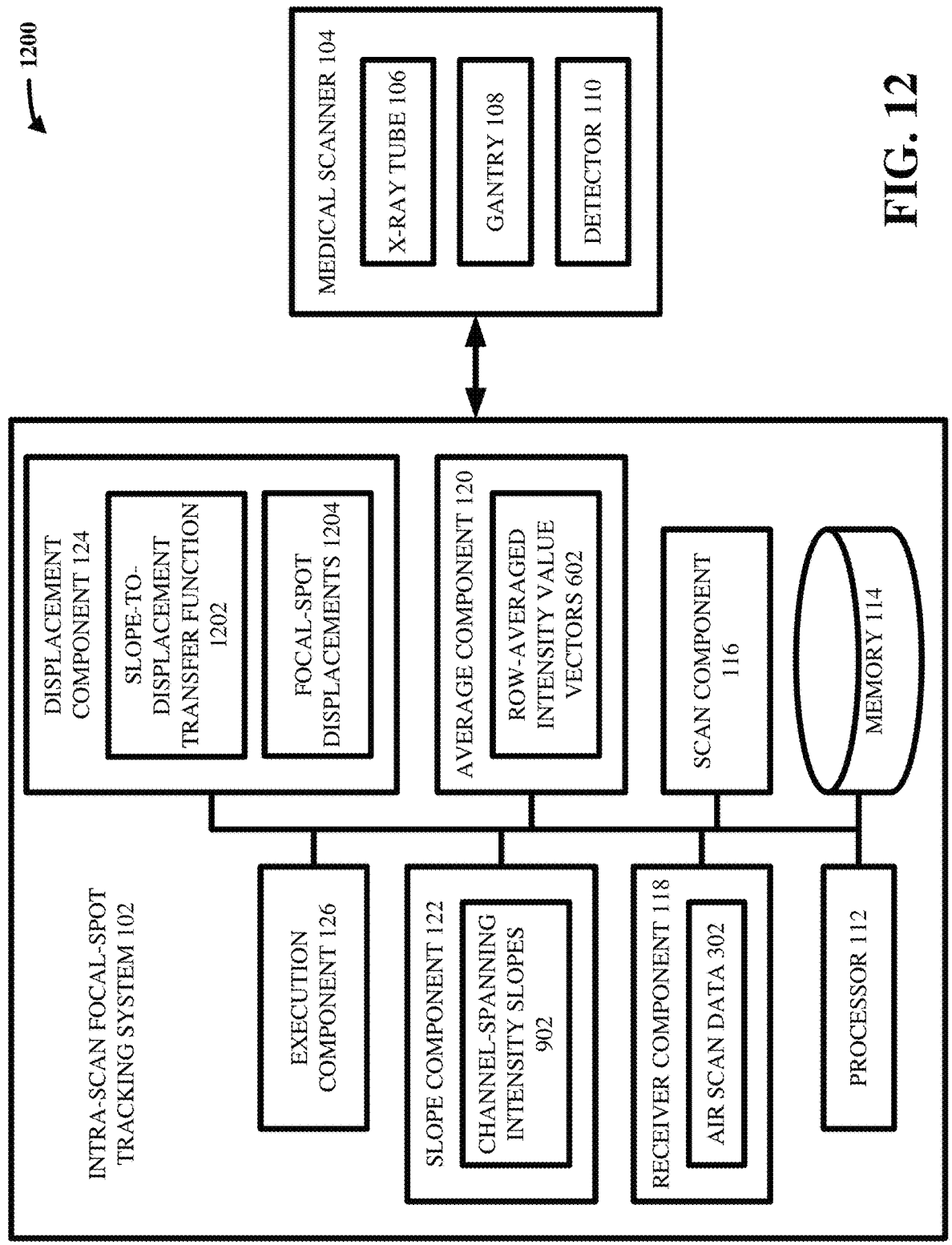
FIG. 12 illustrates a block diagram of an example, non-limiting system including a slope-to-displacement transfer function and/or a set of focal-spot displacements that facilitates low-cost estimation and/or tracking of intra-scan focal-spot displacement in accordance with one or more embodiments described herein.

FIG. 12 illustrates a block diagram of an example, non-limiting system 1200 including a slope-to-displacement transfer function and/or a set of focal-spot displacements that can facilitate low-cost estimation and/or tracking of intra-scan focal-spot displacement in accordance with one or more embodiments described herein. As shown, the system 1200 can, in some cases, comprise the same components as the system 900, and can further comprise a slope-to-displacement transfer function 1202 and/or a set of focal-spot displacements 1204.

In various embodiments, the displacement component 124 can electronically store, electronically maintain, electronically control, and/or otherwise electronically access a slope-to-displacement transfer function 1202. In various aspects, the slope-to-displacement transfer function 1202 can be any suitable mathematical function, and/or combination of mathematical functions, that can take as an input argument a channel-spanning intensity slope (and/or a change in channel-spanning intensity slope) and that can produce as output a focal-spot displacement. Additional details regarding how the slope-to-displacement transfer function 1202 can be identified and/or obtained are discussed with respect to FIG. 18-20.

In any case, the displacement component 124 can electronically generate the set of focal-spot displacements 1204 by applying the slope-to-displacement transfer function 1202 to the set of channel-spanning intensity slopes 902. This is discussed more with respect to FIG. 13.

Figure 13:
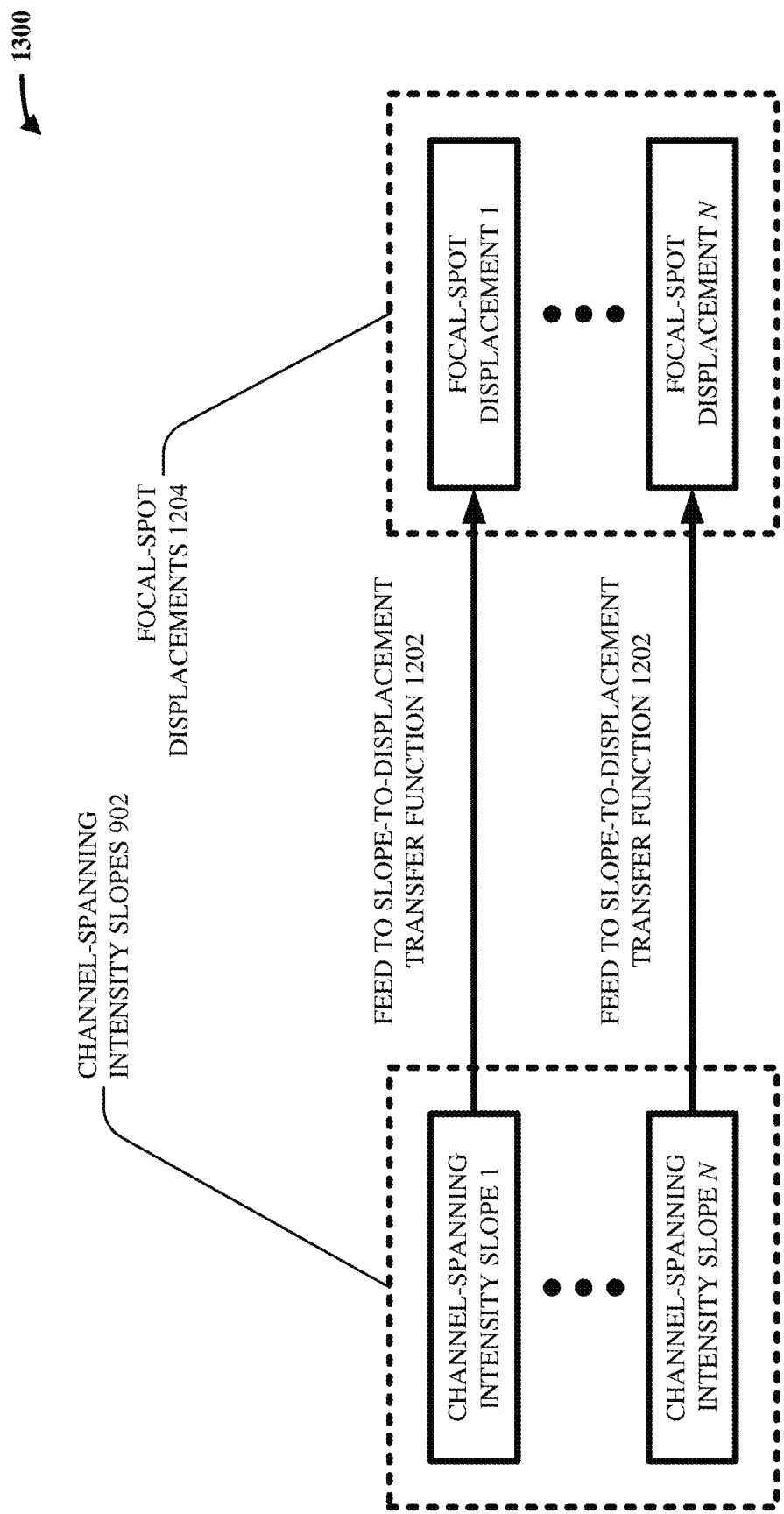
FIG. 13 illustrates an example, non-limiting block diagram showing how a set of focal-spot displacements can be generated from a set of channel-spanning intensity slopes in accordance with one or more embodiments described herein.

FIG. 13 illustrates an example, non-limiting block diagram 1300 showing how the set of focal-spot displacements 1204 can be generated from the set of channel-spanning intensity slopes 902 in accordance with one or more embodiments described herein.

As shown, the set of focal-spot displacements 1204 can correspond (e.g., in one-to-one fashion) with the set of channel-spanning intensity slopes 902. Accordingly, because the set of channel-spanning intensity slopes 902 can include n slopes, the set of focal-spot displacements 1204 can include n displacements: a focal-spot displacement 1 to a focal-spot displacement n. In other words, there can be one focal-spot displacement per channel-spanning intensity slope.

For example, the focal-spot displacement 1 can correspond to the channel-spanning intensity slope 1. That is, the displacement component 124 can electronically compute the focal-spot displacement 1 by feeding the channel-spanning intensity slope 1 to the slope-to-displacement transfer function 1202. Moreover, because the focal-spot displacement 1 can correspond to the channel-spanning intensity slope 1, and because the channel-spanning intensity slope 1 can correspond to the gantry angle 1, the focal-spot displacement 1 can be considered as corresponding to the gantry angle 1. In various cases, the focal-spot displacement 1 can be a scalar that represents a distance, along any suitable axis and/or direction, which distance separates the position of the focal-spot when the X-ray tube 106 is placed according to the gantry angle 1 from a desired and/or predetermined focal-spot position. In other words, the focal-spot displacement 1 can represent how far (e.g., in microns) the focal-spot is from its desired/predetermined location when the X-ray tube 106 is placed at the gantry angle 1.

Likewise, the focal-spot displacement n can correspond to the channel-spanning intensity slope n. That is, the displacement component 124 can electronically compute the focal-spot displacement n by feeding the channel-spanning intensity slope n to the slope-to-displacement transfer function 1202. Just as above, because the focal-spot displacement n can correspond to the channel-spanning intensity slope n, and because the channel-spanning intensity slope n can correspond to the gantry angle n, the focal-spot displacement n can be considered as corresponding to the gantry angle n. In various cases, the focal-spot displacement n can be a scalar that represents a distance, along any suitable axis and/or direction, which distance separates the position of the focal-spot when the X-ray tube 106 is placed according to the gantry angle n from a desired and/or predetermined focal-spot position. In other words, the focal-spot displacement n can represent how far (e.g., in microns) the focal-spot is from its desired/predetermined location when the X-ray tube 106 is placed at the gantry angle n.

Therefore, because the X-ray tube 106 can sweep through the set of gantry angles 402 during a scan (e.g., during the air scan caused by the scan component 116), and because the set of focal-spot displacements 1204 can respectively correspond to the set of gantry angles 402, the set of focal-spot displacements 1204 can be considered as indicating, representing, and/or otherwise conveying the intra-scan motion of the focal-spot of the medical scanner 104 (e.g., can be considered as showing how the focal-spot moves along any suitable axis/dimension as the X-ray tube 106 rotates about/along the gantry 108).

Figure 14:
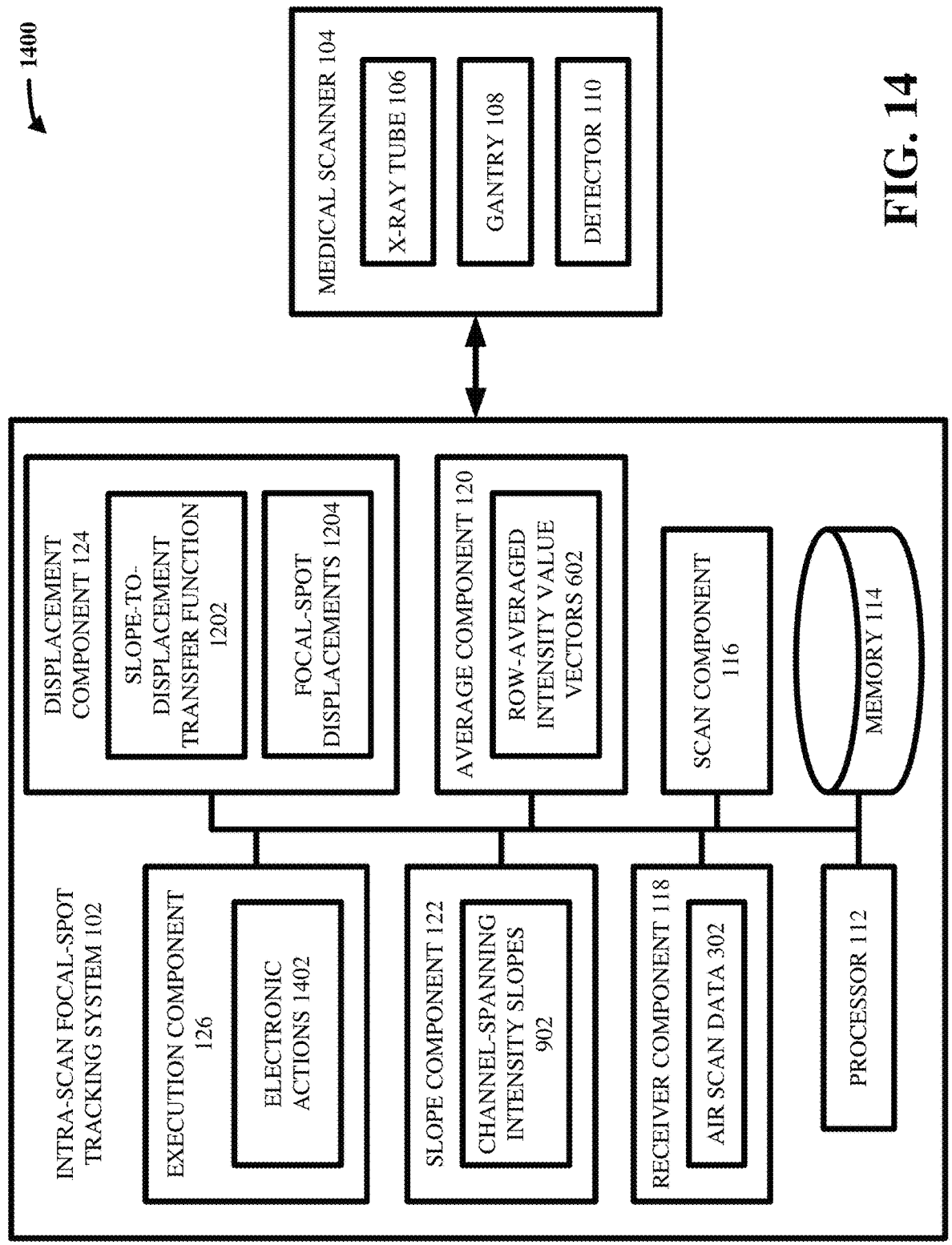
FIG. 14 illustrates a block diagram of an example, non-limiting system including a set of electronic actions that facilitates low-cost estimation and/or tracking of intra-scan focal-spot displacement in accordance with one or more embodiments described herein.

FIG. 14 illustrates a block diagram of an example, non-limiting system 1400 including a set of electronic actions that can facilitate low-cost estimation and/or tracking of intra-scan focal-spot displacement in accordance with one or more embodiments described herein. As shown, the system 1400 can, in some cases, comprise the same components as the system 1200, and can further comprise a set of electronic actions 1402.

In various embodiments, the execution component 126 can electronically perform, cause, initiate, and/or otherwise facilitate the set of electronic actions 1402, based on the set of focal-spot displacements 1204. In various aspects, the set of electronic actions 1402 can include any suitable number of actions that pertain and/or otherwise relate to the set of focal-spot displacements 1204.

As a non-limiting example, the set of electronic actions 1402 can include visually plotting, graphing, and/or rendering the set of focal-spot displacements 1204 against/versus the set of gantry angles 402, on any suitable electronic display, screen, and/or monitor (not shown). In such case, the set of gantry angles 402 can be plotted/graphed along an abscissa direction, and/or the set of focal-spot displacements 1204 can be plotted/graphed along an ordinate direction. In various aspects, a medical professional and/or a technical specialist could visually look at and/or visually inspect such plot/graph, so as to see how the focal-spot of the medical scanner 104 moves and/or changes position as the X-ray tube 106 rotates about/along the gantry 108.

As another non-limiting example, the set of electronic actions 1402 can include comparing the set of focal-spot displacements 1204 with any suitable threshold value and/or generating/transmitting a recommendation to any suitable computing device (not shown) based on such comparison. For instance, the execution component 126 can electronically compare each of the set of focal-spot displacements 1204 with a maximum allowable displacement threshold. If any of the set of focal-spot displacements 1204 exceeds the maximum allowable displacement threshold, then the execution component 126 can electronically generate and/or transmit a message to any suitable computing device (not shown), where such message recommends and/or requests that technical maintenance and/or repairs be performed on the medical scanner 104. In contrast, if none of the set of focal-spot displacements 1204 exceeds the maximum allowable displacement threshold, then the execution component 126 can electronically generate and/or transmit a message to any suitable computing device (not shown), where such message indicates that technical maintenance and/or repairs need not yet be performed on the medical scanner 104.

Figure 15:
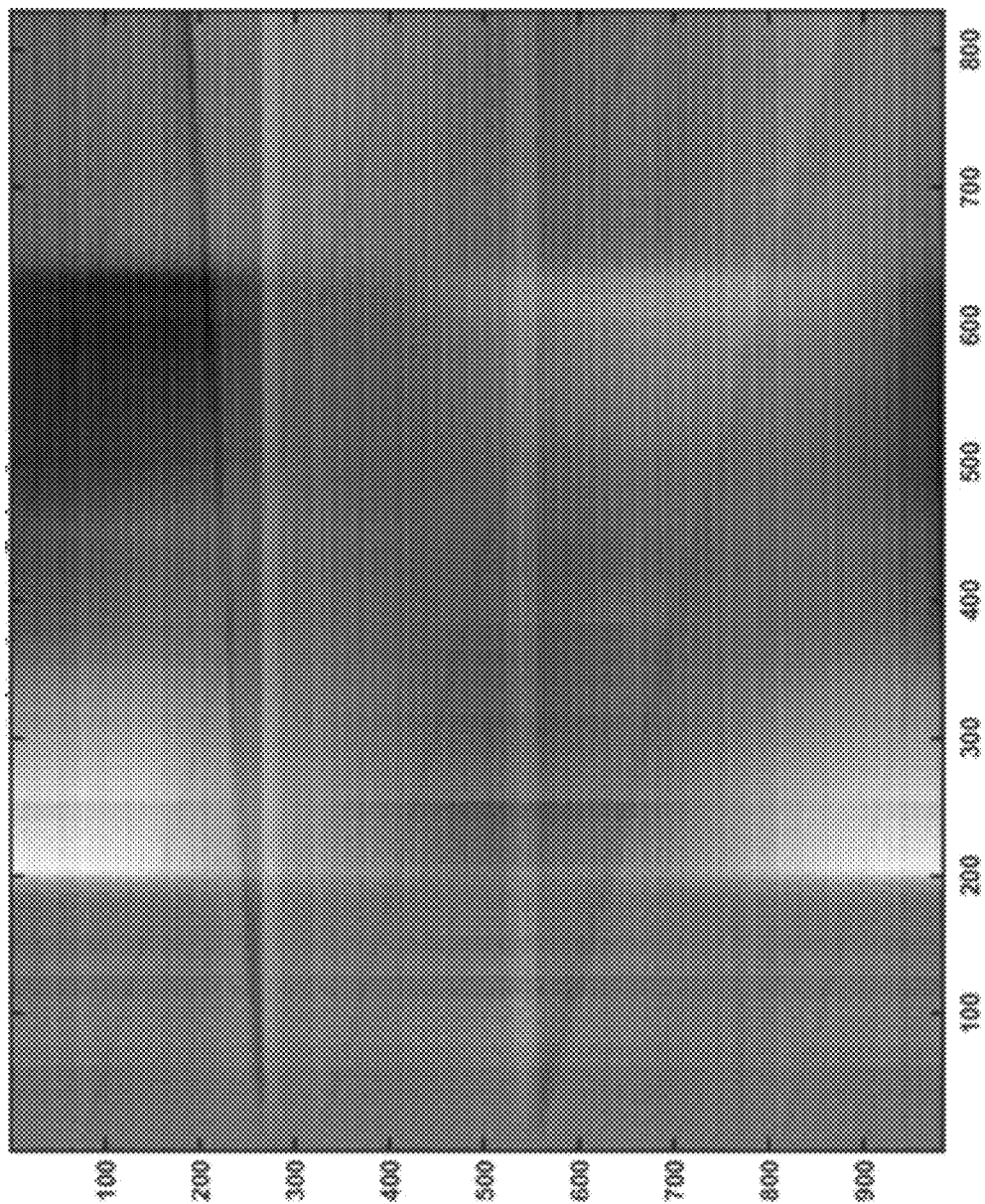
FIGS. 15-17 illustrate non-limiting, example plots in accordance with one or more embodiments described herein.
Figure 16:
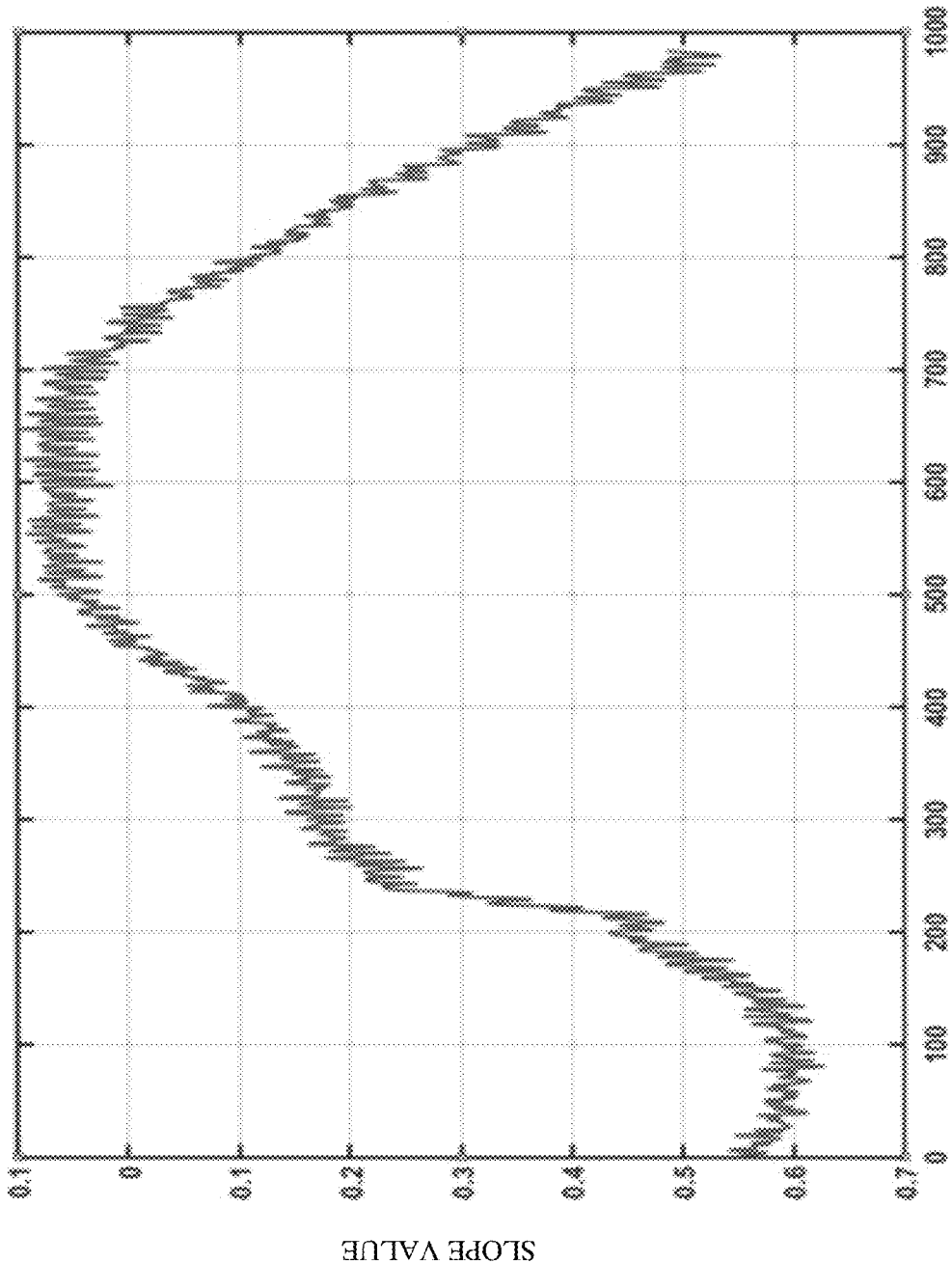
Figure 17:
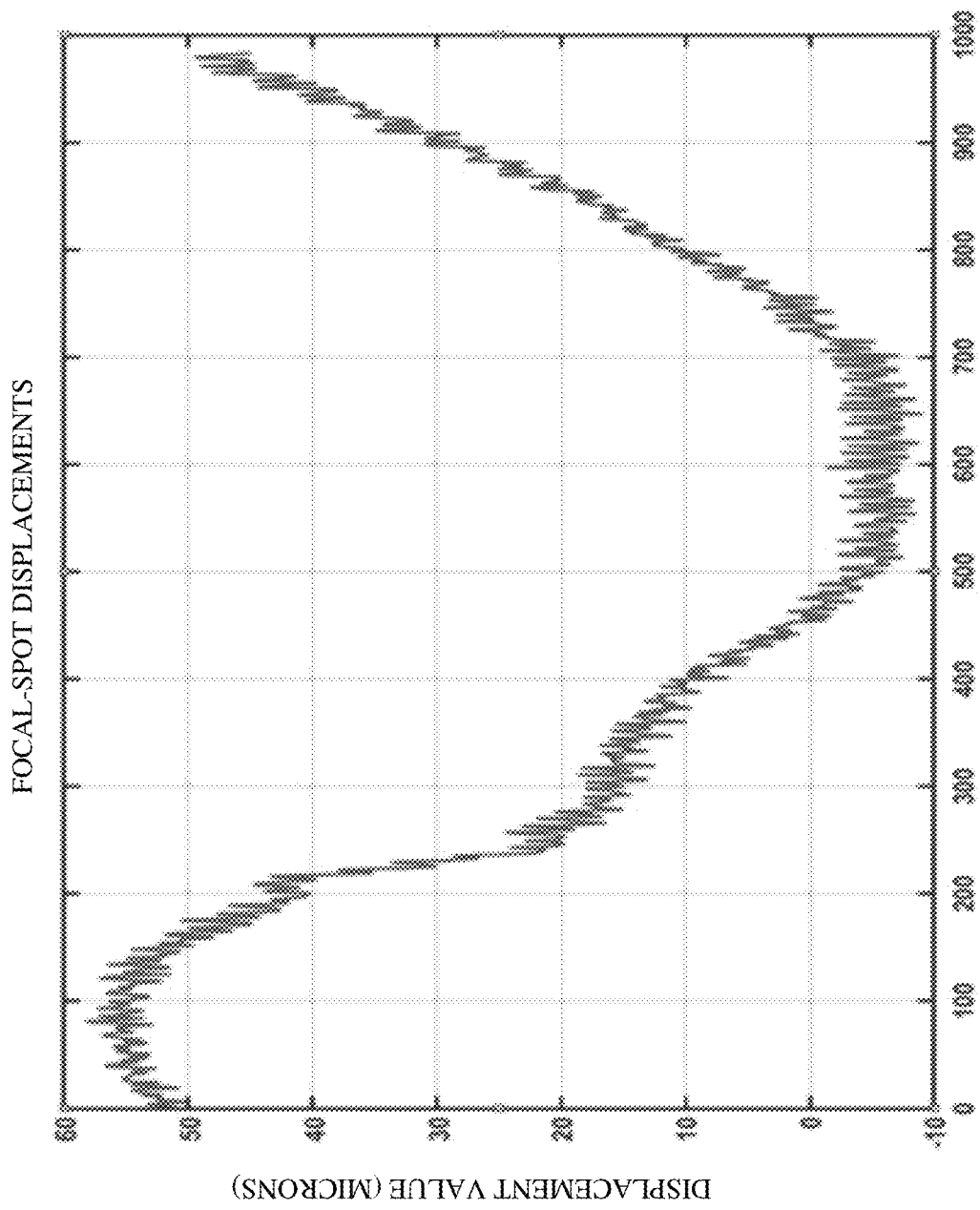

To help clarify various of the above-described details, please consider FIGS. 15-17. FIGS. 15-17 illustrate non-limiting, example plots 1500, 1600, and 1700 in accordance with one or more embodiments described herein.

In various aspects, the present inventors reduced to practice a non-limiting embodiment described herein, in which the medical scanner 104 performed an air scan that included 984 gantry angles, and in which the detector 110 had over 800 channels. In various instances, the plot 1500 visually illustrates, in greyscale, the set of row-averaged intensity value vectors 602 for such non-limiting embodiment. As shown, each of the 984 gantry angles (e.g., referred to as "views" in the FIG. 15) can have a corresponding row-averaged intensity value vector, with each row-averaged intensity value vector having over 800 elements (e.g., one element per channel of the detector 110). In various cases, the plot 1600 visually illustrates the set of channel-spanning intensity slopes 902 for such non-limiting embodiment. As shown, each of the 984 gantry angles (e.g., again referred to as "views") can have a corresponding channel-spanning intensity slope. Although not explicitly shown in FIG. 16, each channel-spanning intensity slope can be considered as having units of $$\frac{\text{Hounsfield Unit}}{\text{Channel}}.$$

In various aspects, the plot 1700 visually illustrates the set of focal-spot displacements 1204 for such non-limiting embodiment. As shown, each of the 984 gantry angles (e.g., again referred to as "views") can have a corresponding focal-spot displacement value, which can be obtained by applying the slope-to-displacement transfer function 1202 to that gantry angle's (e.g., to that view's) corresponding channel-spanning intensity slope.

As described herein, the set of focal-spot displacements 1204, which can describe/represent the intra-scan motion of the focal-spot of the medical scanner 104, can be computed by feeding the set of channel-spanning intensity slopes 902 to the slope-to-displacement transfer function 1202. Thus, in order to facilitate such computation, the slope-to-displacement transfer function 1202 should first be obtained. As mentioned above, the slope-to-displacement transfer function 1202 can be any suitable mathematical function and/or combination of mathematical functions that can take as an input argument a channel-spanning intensity slope (and/or a change in channel-spanning intensity slope) and that can produce as output a focal-spot displacement value. The specific functions (e.g., polynomials, sinusoids, logarithms, exponentials) and/or coefficient values that make up and/or are included in the slope-to-displacement transfer function 1202 can vary depending upon the characteristics of the medical scanner 104. In other words, there can be no universal form of the slope-to-displacement transfer function 1202. Nevertheless, regardless of the characteristics of the medical scanner 104, the slope-to-displacement transfer function 1202 can be universally derived and/or obtained as described with respect to FIGS. 18-20.

Figure 18:
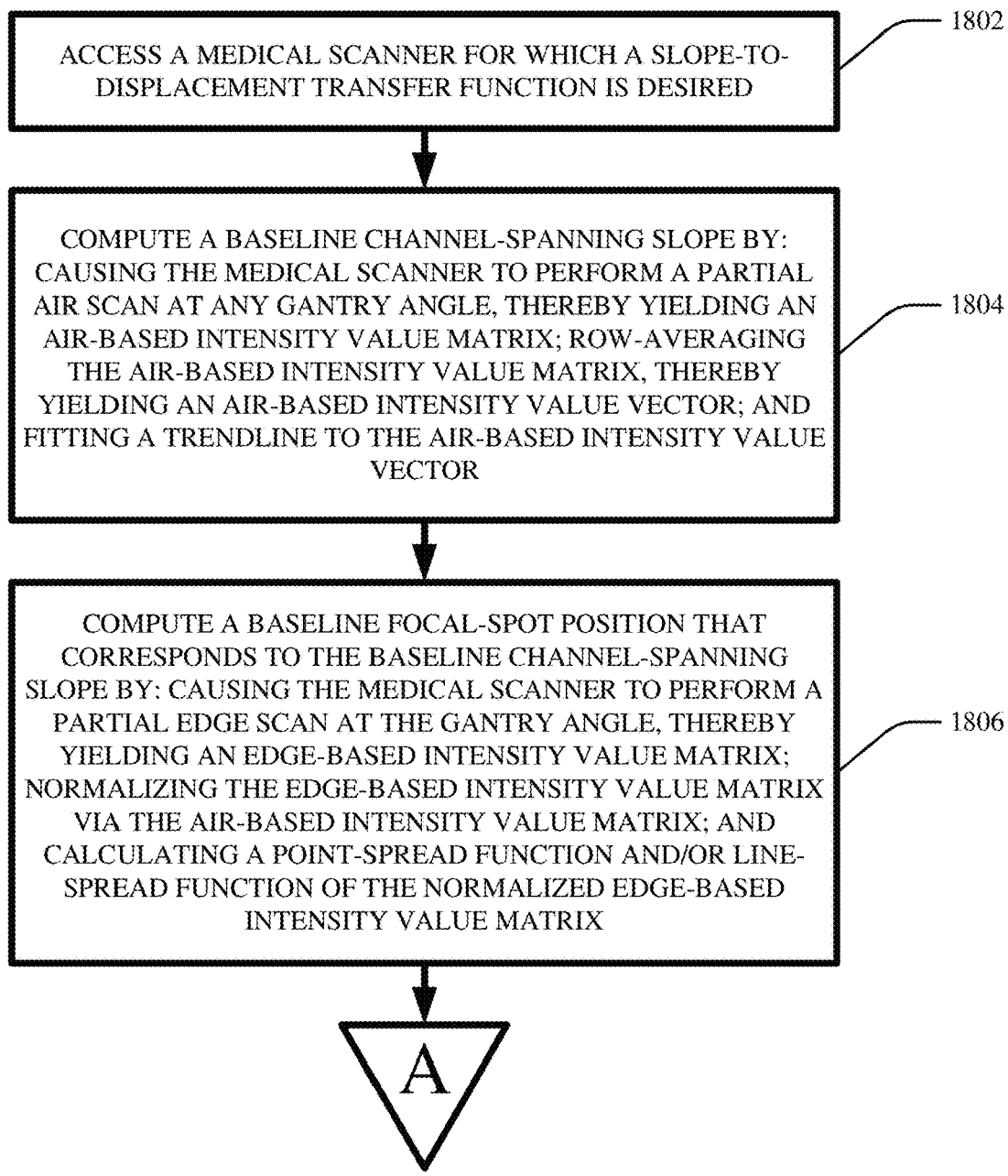
FIGS. 18-20 illustrate flow diagrams of example, non-limiting computer-implemented methods for generating a slope-to-displacement transfer function in accordance with one or more embodiments described herein.
Figure 19:
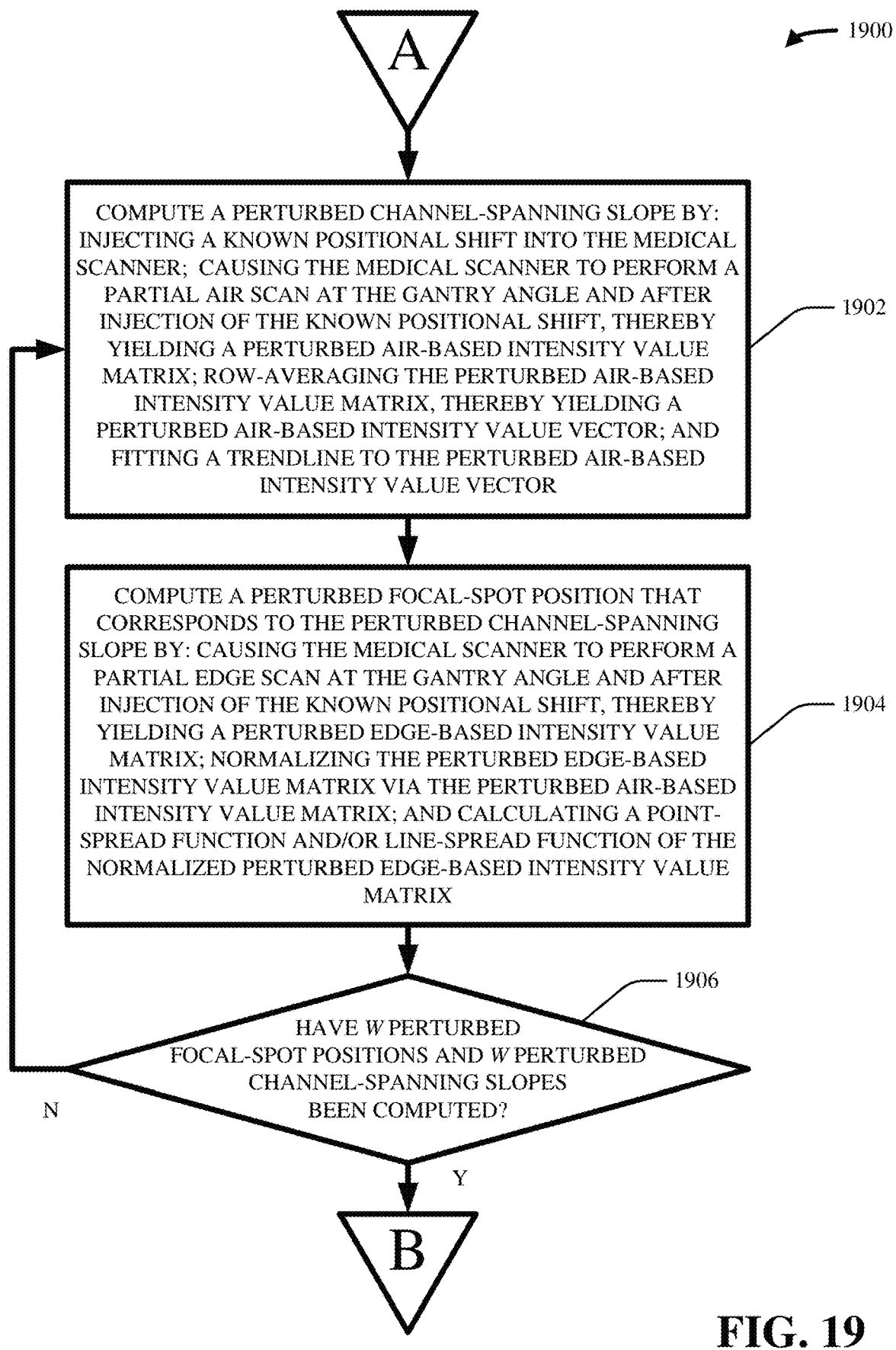
Figure 20:
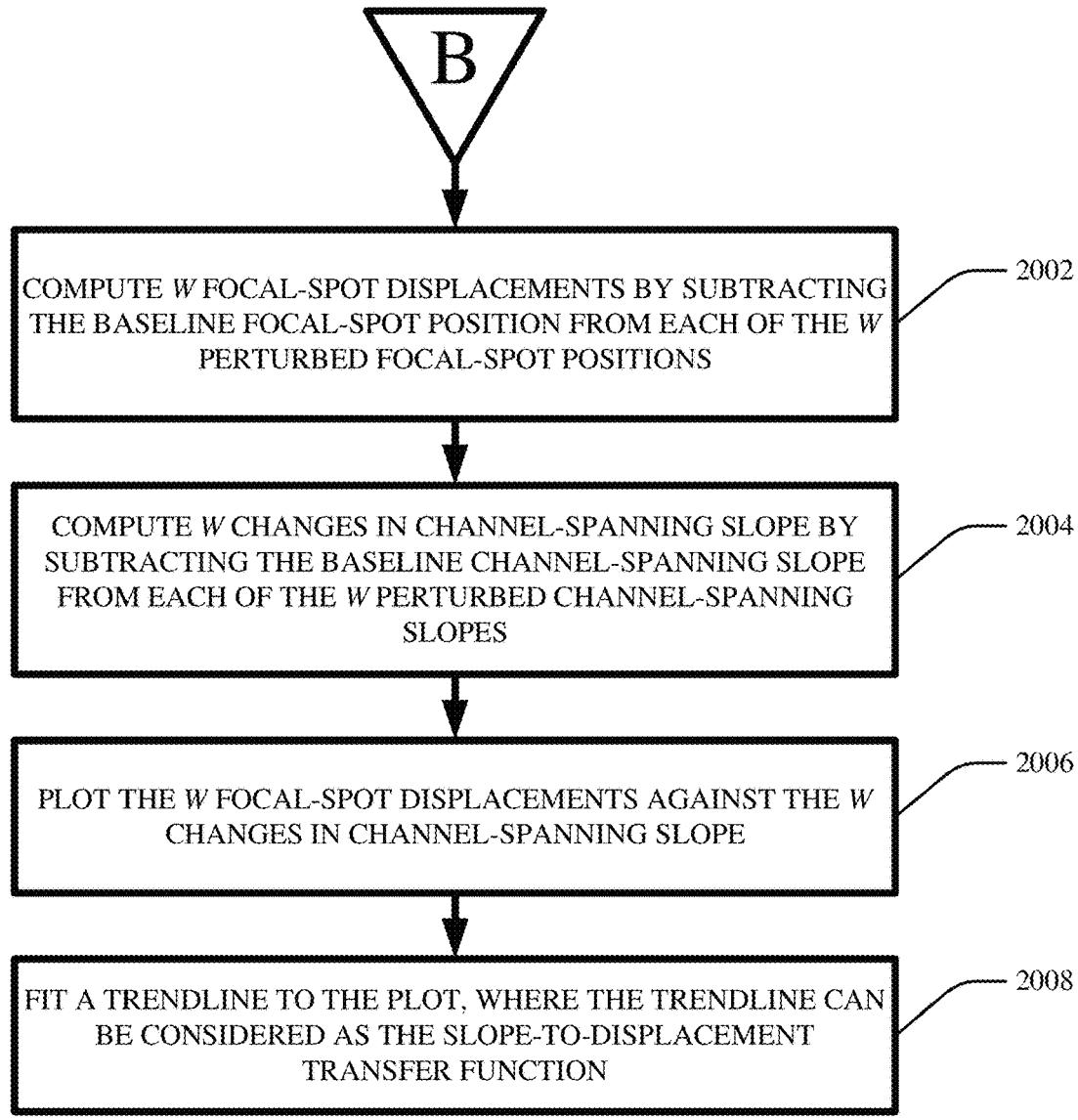

FIGS. 18-20 illustrate flow diagrams of example, non-limiting computer-implemented methods 1800, 1900, and 2000 for generating a slope-to-displacement transfer function in accordance with one or more embodiments described herein.

First, consider the computer-implemented method 1800. In various embodiments, act 1802 can include accessing a medical scanner (e.g., 104) for which a slope-to-displacement transfer function (e.g., 1202) is desired.

In various aspects, act 1804 can include computing a baseline channel-spanning slope for the medical scanner. In various cases, this can be accomplished as follows. First, the medical scanner can perform a partial air scan at any single gantry angle (e.g., a full air scan can sweep through multiple gantry angles, while a partial air scan can be performed at one gantry angle). The result of such partial air scan can be a single intensity value matrix recorded by a multi-channel-multi-row detector (e.g., 110) of the medical scanner. Such intensity value matrix can be referred to as an air-based intensity value matrix. Next, row-averaging can be performed on the air-based intensity value matrix as described above with respect to FIGS. 6-8, thereby yielding an intensity value vector. Such intensity value vector can be referred to as an air-based intensity value vector (e.g., an air-based row-averaged intensity value vector). Lastly, a linear trendline and/or line of best fit can be fitted to the air-based intensity value vector as described above with respect to FIGS. 9-11, and the slope of such linear trendline and/or the slope of such line of best fit can be considered as the baseline channel-spanning slope.

In various instances, act 1806 can include computing a baseline focal-spot position that corresponds to the baseline channel-spanning slope. In various cases, this can be accomplished as follows. First, the medical scanner can perform a partial edge scan at the same gantry angle used to compute the baseline channel-spanning slope (e.g., a full edge scan can sweep through multiple gantry angles, while a partial edge scan can be performed at one gantry angle). The result of such partial edge scan can be a single intensity value matrix recorded by the multi-channel-multi-row detector (e.g., 110) of the medical scanner. Such intensity value matrix can be referred to as an edge-based intensity value matrix. Next, the edge-based intensity value matrix can be normalized via element-wise division with the air-based intensity value matrix. The result of such normalization can be referred to as a normalized edge-based intensity value matrix. Lastly, a line-spread function and/or point-spread function can be derived and/or approximated from the normalized edge-based intensity value matrix. Those having ordinary skill in the art will appreciate how to derive a line-spread function and/or a point-spread function in this way. In various cases, the position of the centroid of the point-spread function can be considered as the baseline focal-spot position.

As shown, the computer-implemented method 1800 can then proceed to act 1902 of the computer-implemented method 1900.

In various embodiments, act 1902 can include computing a perturbed channel-spanning slope for the medical scanner. In various cases, this can be accomplished as follows. First, a known positional shift can be injected into the medical scanner (e.g., the anode and/or cathode of the X-ray tube of the medical scanner can be shifted with respect to each other by any suitable known amount). Then, the medical scanner can perform a partial air scan after the injection of the known positional shift and at the same gantry angle used to compute the baseline channel-spanning slope. The result of such partial air scan can be a single intensity value matrix recorded by the multi-channel-multi-row detector of the medical scanner. Such intensity value matrix can be referred to as a perturbed air-based intensity value matrix. Next, row-averaging can be performed on the perturbed air-based intensity value matrix as described above with respect to FIGS. 6-8, thereby yielding an intensity value vector. Such intensity value vector can be referred to as a perturbed air-based intensity value vector (e.g., a perturbed air-based row-averaged intensity value vector). Lastly, a linear trendline and/or line of best fit can be fitted to the perturbed air-based intensity value vector as described above with respect to FIGS. 9-11, and the slope of such linear trendline and/or the slope of such line of best fit can be considered as the perturbed channel-spanning slope.

In various aspects, act 1904 can include computing a perturbed focal-spot position that corresponds to the perturbed channel-spanning slope. In various cases, this can be accomplished as follows. First, the medical scanner can perform a partial edge scan after the injection of the known positional shift and at the same gantry angle used to compute the baseline channel-spanning slope. The result of such partial edge scan can be a single intensity value matrix recorded by the multi-channel-multi-row detector of the medical scanner. Such intensity value matrix can be referred to as a perturbed edge-based intensity value matrix. Next, the perturbed edge-based intensity value matrix can be normalized via element-wise division with the perturbed air-based intensity value matrix. The result of such normalization can be referred to as a normalized perturbed edge-based intensity value matrix. Lastly, a line-spread function and/or point-spread function can be derived and/or approximated from the normalized perturbed edge-based intensity value matrix. Again, those having ordinary skill in the art will appreciate how to derive a line-spread function and/or a point-spread function in this way. In various cases, the position of the centroid of such point-spread function can be considered as the perturbed focal-spot position.

In various instances, act 1906 can include determining whether w perturbed focal-spot positions and w perturbed channel-spanning slopes have been computed, for any suitable positive integer w. If not, the computer-implemented method 1900 can proceed back to act 1902. If so, the computer-implemented method 1900 can proceed to act 2002 of the computer-implemented method 2000. As can be seen from FIG. 19, acts 1902-1906 can iterate until w pairs of perturbed focal-spot positions and perturbed channel-spanning slopes have been computed. In other words, act 1902-1906 can iterate until w known positional shifts (e.g., which can all be different from each other) have been injected into the medical scanner.

Now, consider the computer-implemented method 2000. In various embodiments, act 2002 can include computing w focal-spot displacements by subtracting the baseline focal-spot position (e.g., computed at act 1806) from each of the w perturbed focal-spot positions (e.g., computed at act 1904).

In various aspects, act 2004 can include computing w changes in channel-spanning slope by subtracting the baseline channel-spanning slope (e.g., computed at act 1804) from each of the w perturbed channel-spanning slopes (e.g., computed at act 1902).

In various instances, act 2006 can include plotting the w focal-spot displacements against the w changes in channel-spanning slope.

In various cases, act 2008 can include fitting a trendline (e.g., linear, quadratic, polynomial, exponential, logarithmic, sinusoidal) to the plot. In various cases, such trendline can be considered as the slope-to-displacement transfer function. In such case, a focal-spot displacement can be computed when given a channel-spanning slope (e.g., one of 902) of the medical scanner by: subtracting the baseline channel-spanning slope (e.g., computed at act 1804) from such given channel-spanning slope; and feeding such difference to the trendline (e.g., to the slope-to-displacement transfer function).

In any case, FIGS. 18-20 explain how the slope-to-displacement transfer function 1202 can be experimentally obtained for the medical scanner 104.

In various embodiments, the particular functions and/or coefficients of the slope-to-displacement transfer function 1202 can depend upon various configurable and/or controllable settings/parameters of the medical scanner 104. For instance, the slope-to-displacement transfer function 1202 can depend upon the anode-cathode voltage and/or amperage of the medical scanner 104, upon the type of filter (e.g., flat versus bowtie) of the medical scanner 104, and/or upon the size (e.g., as measured in microns and/or millimeters) of the focal-spot of the medical scanner 104. Accordingly, in various instances, a unique slope-to-displacement transfer function can be obtained for each unique combination of controllable parameters/settings of the medical scanner 104 (e.g., a first slope-to-displacement transfer function can be obtained when the medical scanner 104 is configured to use a first anode-cathode voltage/amperage, a first filter, and/or a first focal-spot size; a second slope-to-displacement transfer function can be obtained when the medical scanner 104 is configured to use a second anode-cathode voltage/amperage, a second filter, and/or a second focal-spot size). Thus, in various cases, the computer-implemented methods 1800-2000 can be repeated for each unique combination of configurable parameters of the medical scanner 104.

In some cases, a set of slope-to-displacement transfer functions can be available and/or accessible to the displacement component 124 (e.g., due to repeated implementation of FIGS. 18-20), and the displacement component 124 can select from such set the slope-to-displacement transfer function 1202 based on the particular and/or current configurable parameters of the medical scanner 104.

Figure 21:
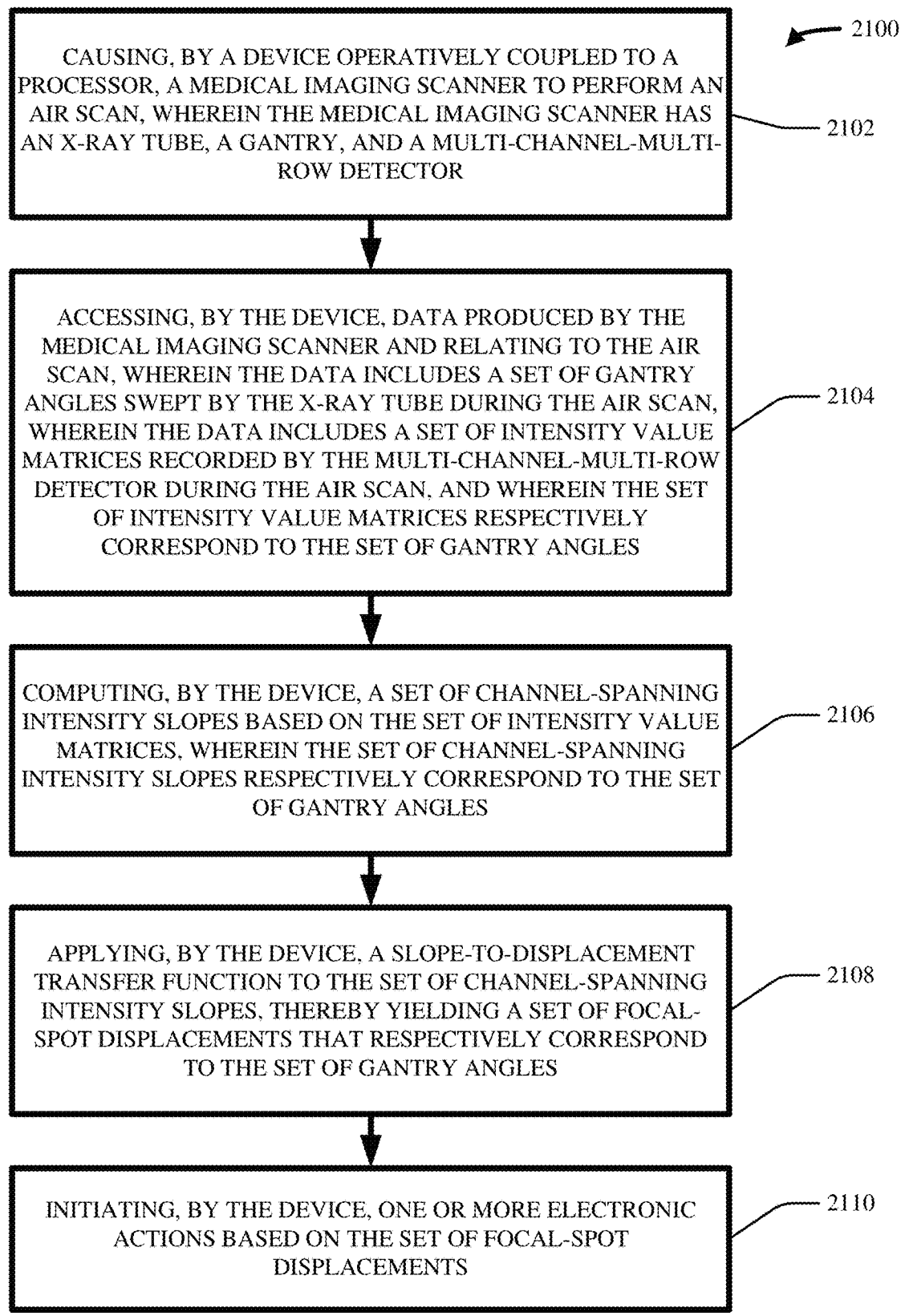
FIG. 21 illustrates a flow diagram of an example, non-limiting computer-implemented method that facilitates low-cost estimation and/or tracking of intra-scan focal-spot displacement in accordance with one or more embodiments described herein.

FIG. 21 illustrates a flow diagram of an example, non-limiting computer-implemented method 2100 that can facilitate low-cost estimation and/or tracking of intra-scan focal-spot displacement in accordance with one or more embodiments described herein. In various cases, the intra-scan focal-spot tracking system 102 can facilitate the computer-implemented method 2100.

In various embodiments, act 2102 can include causing, by a device (e.g., via 116) operatively coupled to a processor, a medical imaging scanner (e.g., 104) to perform an air scan, wherein the medical imaging scanner has an X-ray tube (e.g., 106), a gantry (e.g., 108), and/or a multi-channel-multi-row detector (e.g., 110).

In various aspects, act 2104 can include accessing, by the device (e.g., via 118), data (e.g., 302) produced by the medical imaging scanner and relating to the air scan. In various cases, the data can include a set of gantry angles (e.g., 402) swept by the X-ray tube during the air scan. Moreover, the data can include a set of intensity value matrices (e.g., 404) recorded by the multi-channel-multi-row detector during the air scan. In various cases, the set of intensity value matrices can respectively correspond to the set of gantry angles.

In various instances, act 2106 can include computing, by the device (e.g., via 122), a set of channel-spanning intensity slopes (e.g., 902) based on the set of intensity value matrices. In various cases, the set of channel-spanning intensity slopes can respectively correspond to the set of gantry angles.

In various aspects, act 2108 can include applying, by the device (e.g., via 124), a slope-to-displacement transfer function (e.g., 1202) to the set of channel-spanning intensity slopes, thereby yielding a set of focal-spot displacements (e.g., 1204) that respectively correspond to the set of gantry angles.

In various instances, 2110 can include initiating, by the device (e.g., via 126), one or more electronic actions (e.g., 1402) based on the set of focal-spot displacements.

Although not explicitly shown in FIG. 21, the one or more electronic actions can include plotting, by the device (e.g., via 126) and on an electronic display, the set of focal-spot displacements against the set of gantry angles (e.g., as show with respect to FIG. 17).

Although not explicitly shown in FIG. 21, the one or more electronic actions can include transmitting, by the device (e.g., via 126), a recommendation that the medical imaging scanner should undergo maintenance, in response to a determination that the set of focal-spot displacements fail to satisfy at least one threshold.

Although not explicitly shown in FIG. 21, the computer-implemented method 2100 can further include: computing, by the device (e.g., via 120), a set of row-averaged intensity value vectors (e.g., 602) based on the set of intensity value matrices, wherein the set of row-averaged intensity value vectors can respectively correspond to the set of gantry angles. In various cases, the computing the set of channel-spanning intensity slopes can be based on applying a trend-line technique to the set of row-averaged intensity value vectors across a channel interval (e.g., as explained with respect to FIGS. 9-11).

Although not explicitly shown in FIG. 21, the computer-implemented method 2100 can further include selecting, by the device (e.g., via 124), the slope-to-displacement transfer function from a set of available transfer functions, based on one or more configurable parameters of the medical imaging scanner. In various cases, the one or more configurable parameters can include an anode-cathode voltage of the X-ray tube, an anode-cathode current of the X-ray tube, a type of filter of the X-ray tube, and/or a focal-spot size of the X-ray tube.

Although not explicitly shown in FIG. 21, the slope-to-displacement transfer function can be estimated based on a plurality of focal-spot positional perturbations injected into the X-ray tube (e.g., as explained with respect to FIGS. 18-20).

Therefore, various embodiments described herein include a computerized tool that can estimate and/or track, in low-cost and/or low-burden fashion, the intra-scan motion of a focal-spot of a medical scanner, by leveraging channel-spanning intensity slopes. Such a technique can be considered as far more efficient as compared to performing a tungsten edge scan at every possible gantry angle of the medical scanner. Certainly then, such a computerized tool qualifies as a useful and practical application of computers.

In various instances, machine learning algorithms and/or models can be implemented in any suitable way to facilitate any suitable aspects described herein. To facilitate some of the above-described machine learning aspects of various embodiments of the subject innovation, consider the following discussion of artificial intelligence (AI). Various embodiments of the present innovation herein can employ artificial intelligence to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, zn)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Those having ordinary skill in the art will appreciate that the herein disclosure describes non-limiting examples of various embodiments of the subject innovation. For ease of description and/or explanation, various portions of the herein disclosure utilize the term "each" when discussing various embodiments of the subject innovation. Those having ordinary skill in the art will appreciate that such usages of the term "each" are non-limiting examples. In other words, when the herein disclosure provides a description that is applied to "each" of some particular object and/or component, it should be understood that this is a non-limiting example of various embodiments of the subject innovation, and it should be further understood that, in various other embodiments of the subject innovation, it can be the case that such description applies to fewer than "each" of that particular object and/or component.

Figure 22:
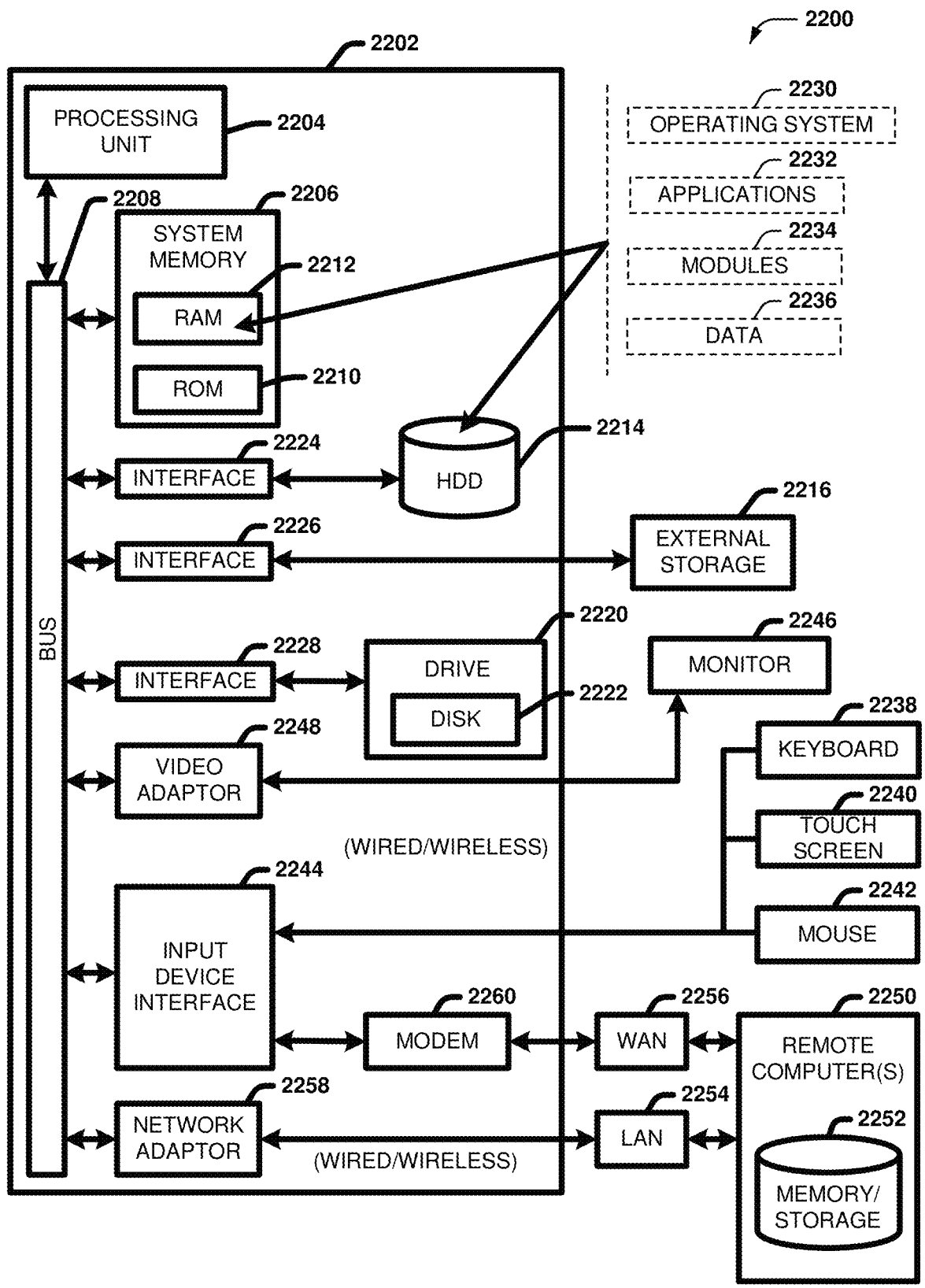
FIG. 22 illustrates a block diagram of an example, non-limiting operating environment in which one or more embodiments described herein can be facilitated.

In order to provide additional context for various embodiments described herein, FIG. 22 and the following discussion are intended to provide a brief, general description of a suitable computing environment 2200 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 22, the example environment 2200 for implementing various embodiments of the aspects described herein includes a computer 2202, the computer 2202 including a processing unit 2204, a system memory 2206 and a system bus 2208. The system bus 2208 couples system components including, but not limited to, the system memory 2206 to the processing unit 2204. The processing unit 2204 can be any of various commercially available processors. Dual microprocessors and other multi-processor architectures can also be employed as the processing unit 2204.

The system bus 2208 can be any of several types of bus structure that can further interconnect to a memory bus (with or without a memory controller), a peripheral bus, and a local bus using any of a variety of commercially available bus architectures. The system memory 2206 includes ROM 2210 and RAM 2212. A basic input/output system (BIOS) can be stored in a non-volatile memory such as ROM, erasable programmable read only memory (EPROM), EEPROM, which BIOS contains the basic routines that help to transfer information between elements within the computer 2202, such as during startup. The RAM 2212 can also include a high-speed RAM such as static RAM for caching data.

The computer 2202 further includes an internal hard disk drive (HDD) 2214 (e.g., EIDE, SATA), one or more external storage devices 2216 (e.g., a magnetic floppy disk drive (FDD) 2216, a memory stick or flash drive reader, a memory card reader, etc.) and a drive 2220, e.g., such as a solid state drive, an optical disk drive, which can read or write from a disk 2222, such as a CD-ROM disc, a DVD, a BD, etc. Alternatively, where a solid state drive is involved, disk 2222 would not be included, unless separate. While the internal HDD 2214 is illustrated as located within the computer 2202, the internal HDD 2214 can also be configured for external use in a suitable chassis (not shown). Additionally, while not shown in environment 2200, a solid state drive (SSD) could be used in addition to, or in place of, an HDD 2214. The HDD 2214, external storage device(s) 2216 and drive 2220 can be connected to the system bus 2208 by an HDD interface 2224, an external storage interface 2226 and a drive interface 2228, respectively. The interface 2224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2212, including an operating system 2230, one or more application programs 2232, other program modules 2234 and program data 2236. All or portions of the operating system, applications, modules, and/or data can also be cached in the RAM 2212. The systems and methods described herein can be implemented utilizing various commercially available operating systems or combinations of operating systems.

Computer 2202 can optionally comprise emulation technologies. For example, a hypervisor (not shown) or other intermediary can emulate a hardware environment for operating system 2230, and the emulated hardware can optionally be different from the hardware illustrated in FIG. 22. In such an embodiment, operating system 2230 can comprise one virtual machine (VM) of multiple VMs hosted at computer 2202. Furthermore, operating system 2230 can provide runtime environments, such as the Java runtime environment or the .NET framework, for applications 2232. Runtime environments are consistent execution environments that allow applications 2232 to run on any operating system that includes the runtime environment. Similarly, operating system 2230 can support containers, and applications 2232 can be in the form of containers, which are lightweight, standalone, executable packages of software that include, e.g., code, runtime, system tools, system libraries and settings for an application.

Further, computer 2202 can be enable with a security module, such as a trusted processing module (TPM). For instance with a TPM, boot components hash next in time boot components, and wait for a match of results to secured values, before loading a next boot component. This process can take place at any layer in the code execution stack of computer 2202, e.g., applied at the application execution level or at the operating system (OS) kernel level, thereby enabling security at any level of code execution.

A user can enter commands and information into the computer 2202 through one or more wired/wireless input devices, e.g., a keyboard 2238, a touch screen 2240, and a pointing device, such as a mouse 2242. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2204 through an input device interface 2244 that can be coupled to the system bus 2208, but can be connected by other interfaces, such as a parallel port, an IEEE 1394 serial port, a game port, a USB port, an IR interface, a BLUETOOTH® interface, etc.

A monitor 2246 or other type of display device can be also connected to the system bus 2208 via an interface, such as a video adapter 2248. In addition to the monitor 2246, a computer typically includes other peripheral output devices (not shown), such as speakers, printers, etc.

The computer 2202 can operate in a networked environment using logical connections via wired and/or wireless communications to one or more remote computers, such as a remote computer(s) 2250. The remote computer(s) 2250 can be a workstation, a server computer, a router, a personal computer, portable computer, microprocessor-based entertainment appliance, a peer device or other common network node, and typically includes many or all of the elements described relative to the computer 2202, although, for purposes of brevity, only a memory/storage device 2252 is illustrated. The logical connections depicted include wired/wireless connectivity to a local area network (LAN) 2254 and/or larger networks, e.g., a wide area network (WAN) 2256. Such LAN and WAN networking environments are commonplace in offices and companies, and facilitate enterprise-wide computer networks, such as intranets, all of which can connect to a global communications network, e.g., the Internet.

When used in a LAN networking environment, the computer 2202 can be connected to the local network 2254 through a wired and/or wireless communication network interface or adapter 2258. The adapter 2258 can facilitate wired or wireless communication to the LAN 2254, which can also include a wireless access point (AP) disposed thereon for communicating with the adapter 2258 in a wireless mode.

When used in a WAN networking environment, the computer 2202 can include a modem 2260 or can be connected to a communications server on the WAN 2256 via other means for establishing communications over the WAN 2256, such as by way of the Internet. The modem 2260, which can be internal or external and a wired or wireless device, can be connected to the system bus 2208 via the input device interface 2244. In a networked environment, program modules depicted relative to the computer 2202 or portions thereof, can be stored in the remote memory/storage device 2252. It will be appreciated that the network connections shown are example and other means of establishing a communications link between the computers can be used.

When used in either a LAN or WAN networking environment, the computer 2202 can access cloud storage systems or other network-based storage systems in addition to, or in place of, external storage devices 2216 as described above, such as but not limited to a network virtual machine providing one or more aspects of storage or processing of information. Generally, a connection between the computer 2202 and a cloud storage system can be established over a LAN 2254 or WAN 2256 e.g., by the adapter 2258 or modem 2260, respectively. Upon connecting the computer 2202 to an associated cloud storage system, the external storage interface 2226 can, with the aid of the adapter 2258 and/or modem 2260, manage storage provided by the cloud storage system as it would other types of external storage. For instance, the external storage interface 2226 can be configured to provide access to cloud storage sources as if those sources were physically connected to the computer 2202.

The computer 2202 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 23:
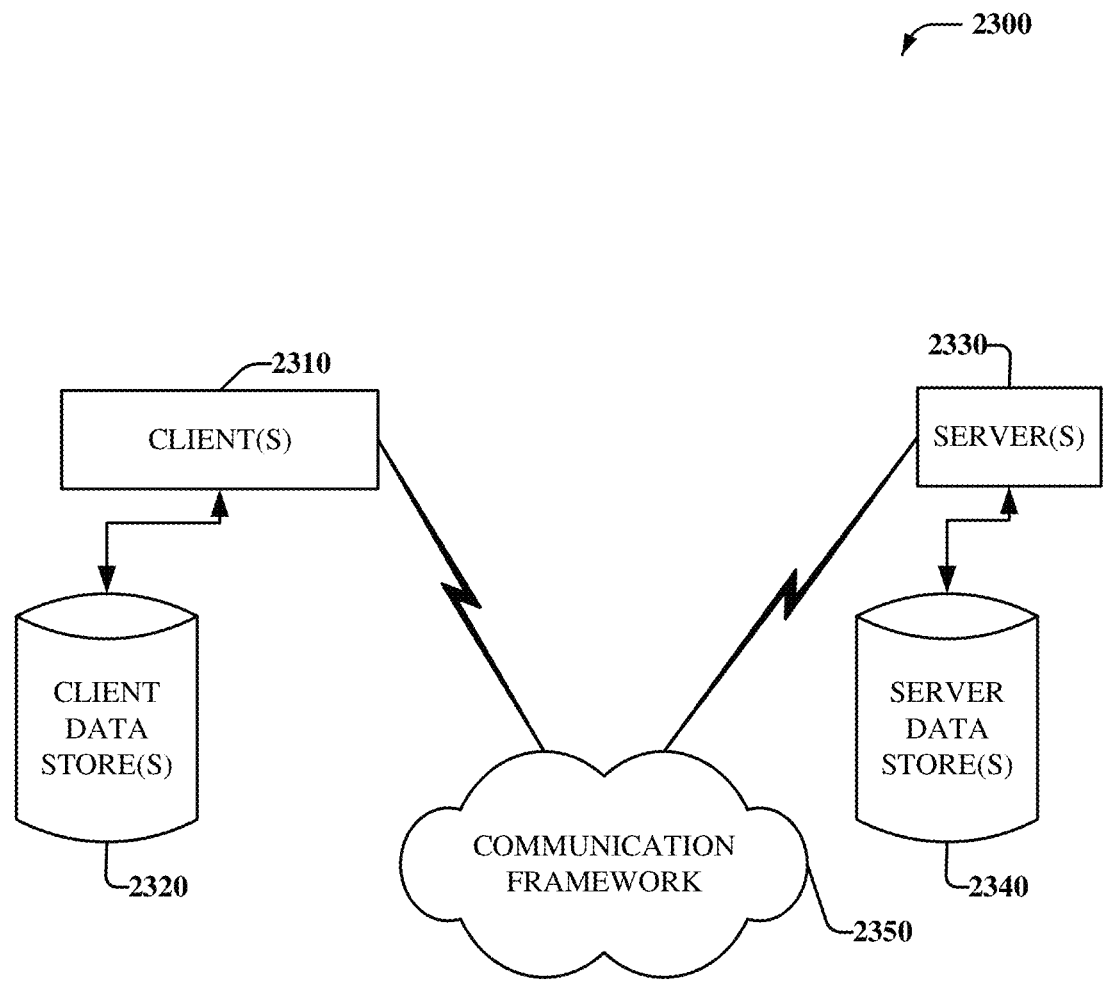
FIG. 23 illustrates an example networking environment operable to execute various implementations described herein.

FIG. 23 is a schematic block diagram of a sample computing environment 2300 with which the disclosed subject matter can interact. The sample computing environment 2300 includes one or more client(s) 2310. The client(s) 2310 can be hardware and/or software (e.g., threads, processes, computing devices). The sample computing environment 2300 also includes one or more server(s) 2330. The server(s) 2330 can also be hardware and/or software (e.g., threads, processes, computing devices). The servers 2330 can house threads to perform transformations by employing one or more embodiments as described herein, for example. One possible communication between a client 2310 and a server 2330 can be in the form of a data packet adapted to be transmitted between two or more computer processes. The sample computing environment 2300 includes a communication framework 2350 that can be employed to facilitate communications between the client(s) 2310 and the server(s) 2330. The client(s) 2310 are operably connected to one or more client data store(s) 2320 that can be employed to store information local to the client(s) 2310. Similarly, the server(s) 2330 are operably connected to one or more server data store(s) 2340 that can be employed to store information local to the servers 2330.

Various embodiments described herein may be a system, a method, an apparatus and/or a computer program product at any possible technical detail level of integration. The computer program product can include a computer readable storage medium (or media) having computer readable program instructions thereon for causing a processor to carry out aspects of various embodiments described herein. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments described herein can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of various embodiments described herein.

Aspects of various embodiments are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a processor that executes computer-executable components stored in a computer-readable memory, the computer-executable components comprising:
   a scan component that causes a medical imaging scanner to perform an air scan, wherein the medical imaging scanner has an X-ray tube, a gantry, and a multi-channel-multi-row detector;
   a receiver component that accesses data produced by the medical imaging scanner and relating to the air scan, wherein the data includes a set of gantry angles swept by the X-ray tube during the air scan, wherein the data includes a set of intensity value matrices recorded by the multi-channel-multi-row detector during the air scan, and wherein the set of intensity value matrices respectively correspond to the set of gantry angles;
   a slope component that computes a set of channel-spanning intensity slopes based on the set of intensity value matrices, wherein the set of channel-spanning intensity slopes respectively correspond to the set of gantry angles;
   a displacement component that applies a slope-to-displacement transfer function to the set of channel-spanning intensity slopes, thereby yielding a set of focal-spot displacements that respectively correspond to the set of gantry angles; and
   an execution component that initiates one or more electronic actions based on the set of focal-spot displacements.

2. The system of claim 1, wherein the one or more electronic actions include plotting, on an electronic display, the set of focal-spot displacements against the set of gantry angles.

3. The system of claim 1, wherein the one or more electronic actions include transmitting a recommendation that the medical imaging scanner should undergo maintenance, in response to a determination that the set of focal-spot displacements fail to satisfy at least one threshold.

4. The system of claim 1, wherein the computer-executable components further comprise:
an average component that computes a set of row-averaged intensity value vectors based on the set of intensity value matrices, wherein the set of row-averaged intensity value vectors respectively correspond to the set of gantry angles, and wherein the slope component computes the set of channel-spanning intensity slopes by applying a trendline technique to the set of row-averaged intensity value vectors across a channel interval.

5. The system of claim 1, wherein the displacement component selects the slope-to-displacement transfer function from a set of available transfer functions, based on one or more configurable parameters of the medical imaging scanner.

6. The system of claim 5, wherein the one or more configurable parameters include an anode-cathode voltage of the X-ray tube, an anode-cathode current of the X-ray tube, a type of filter of the X-ray tube, or a focal-spot size of the X-ray tube.

7. The system of claim 1, wherein the slope-to-displacement transfer function is estimated based on a plurality of focal-spot positional perturbations injected into the X-ray tube.

8. A computer-implemented method, comprising:
causing, by a device operatively coupled to a processor, a medical imaging scanner to perform an air scan, wherein the medical imaging scanner has an X-ray tube, a gantry, and a multi-channel-multi-row detector;
accessing, by the device, data produced by the medical imaging scanner and relating to the air scan, wherein the data includes a set of gantry angles swept by the X-ray tube during the air scan, wherein the data includes a set of intensity value matrices recorded by the multi-channel-multi-row detector during the air scan, and wherein the set of intensity value matrices respectively correspond to the set of gantry angles;
computing, by the device, a set of channel-spanning intensity slopes based on the set of intensity value matrices, wherein the set of channel-spanning intensity slopes respectively correspond to the set of gantry angles;
applying, by the device, a slope-to-displacement transfer function to the set of channel-spanning intensity slopes, thereby yielding a set of focal-spot displacements that respectively correspond to the set of gantry angles; and
initiating, by the device, one or more electronic actions based on the set of focal-spot displacements.

9. The computer-implemented method of claim 8, wherein the one or more electronic actions include plotting, by the device and on an electronic display, the set of focal-spot displacements against the set of gantry angles.

10. The computer-implemented method of claim 8, wherein the one or more electronic actions include transmitting, by the device, a recommendation that the medical imaging scanner should undergo maintenance, in response to a determination that the set of focal-spot displacements fail to satisfy at least one threshold.

11. The computer-implemented method of claim 8, further comprising:
computing, by the device, a set of row-averaged intensity value vectors based on the set of intensity value matrices, wherein the set of row-averaged intensity value vectors respectively correspond to the set of gantry angles, and wherein the computing the set of channel-spanning intensity slopes is based on applying a trendline technique to the set of row-averaged intensity value vectors across a channel interval.

12. The computer-implemented method of claim 8, further comprising:
selecting, by the device, the slope-to-displacement transfer function from a set of available transfer functions, based on one or more configurable parameters of the medical imaging scanner.

13. The computer-implemented method of claim 12, wherein the one or more configurable parameters include an anode-cathode voltage of the X-ray tube, an anode-cathode current of the X-ray tube, a type of filter of the X-ray tube, or a focal-spot size of the X-ray tube.

14. The computer-implemented method of claim 8, wherein the slope-to-displacement transfer function is estimated based on a plurality of focal-spot positional perturbations injected into the X-ray tube.

15. A computer program product for facilitating low-cost estimation and/or tracking of intra-scan focal-spot displacement, the computer program product comprising a computer-readable memory having program instructions embodied therewith, the program instructions executable by a processor to cause the processor to:
cause a medical imaging scanner to perform an air scan, wherein the medical imaging scanner has an X-ray tube, a gantry, and a multi-channel-multi-row detector;
access data produced by the medical imaging scanner and relating to the air scan, wherein the data includes a set of gantry angles swept by the X-ray tube during the air scan, wherein the data includes a set of intensity value matrices recorded by the multi-channel-multi-row detector during the air scan, and wherein the set of intensity value matrices respectively correspond to the set of gantry angles;
compute a set of channel-spanning intensity slopes based on the set of intensity value matrices, wherein the set of channel-spanning intensity slopes respectively correspond to the set of gantry angles;
apply a slope-to-displacement transfer function to the set of channel-spanning intensity slopes, thereby yielding a set of focal-spot displacements that respectively correspond to the set of gantry angles; and
initiate one or more electronic actions based on the set of focal-spot displacements.

16. The computer program product of claim 15, wherein the one or more electronic actions include plotting, on an electronic display, the set of focal-spot displacements against the set of gantry angles.

17. The computer program product of claim 15, wherein the one or more electronic actions include transmitting a recommendation that the medical imaging scanner undergo maintenance, in response to a determination that the set of focal-spot displacements fail to satisfy at least one threshold.

18. The computer program product of claim 15, wherein the program instructions are further executable to cause the processor to:
compute a set of row-averaged intensity value vectors based on the set of intensity value matrices, wherein the set of row-averaged intensity value vectors respectively correspond to the set of gantry angles, and wherein the processor computes the set of channel-spanning intensity slopes by applying a trendline technique to the set of row-averaged intensity value vectors across a channel interval.

19. The computer program product of claim 15, wherein the program instructions are further executable to cause the processor to:

select the slope-to-displacement transfer function from a set of available transfer functions, based on one or more configurable parameters of the medical imaging scanner.

20. The computer program product of claim 19, wherein the one or more configurable parameters include an anode-cathode voltage of the X-ray tube, an anode-cathode current of the X-ray tube, a type of filter of the X-ray tube, or a focal-spot size of the X-ray tube.

* * * * *